United States Patent
Kopperschmidt et al.

(10) Patent No.: US 11,490,970 B2
(45) Date of Patent: Nov. 8, 2022

(54) AUTOMATIC CANNULATING MACHINE

(71) Applicant: FRESENIUS MEDICAL CARE DEUTSCHLAND GMBH, Bad Homburg (DE)

(72) Inventors: Pascal Kopperschmidt, Dittelbrunn (DE); Pia Daniel, Bodman (DE); Reiner Spickermann, Wasserlosen-Burghausen (DE); Otto Arkossy, Budapest (HU); Cacilia Scholz, Schwalbach (DE); Kai-Uwe Ritter, Rednitz-Hembach (DE); Elke Schulte, Schweinfurt (DE); Christopher Hauke, Mainz-Kostheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 697 days.

(21) Appl. No.: 16/479,940

(22) PCT Filed: Jan. 29, 2018

(86) PCT No.: PCT/EP2018/052124
§ 371 (c)(1),
(2) Date: Jul. 23, 2019

(87) PCT Pub. No.: WO2018/138333
PCT Pub. Date: Aug. 2, 2018

(65) Prior Publication Data
US 2019/0374700 A1   Dec. 12, 2019

(30) Foreign Application Priority Data
Jan. 30, 2017   (DE) .................... 10 2017 201 434.2

(51) Int. Cl.
A61B 34/30     (2016.01)
A61M 1/36      (2006.01)
(Continued)

(52) U.S. Cl.
CPC .............. *A61B 34/30* (2016.02); *A61B 34/20* (2016.02); *A61B 90/50* (2016.02); *A61M 1/3655* (2013.01);
(Continued)

(58) Field of Classification Search
CPC ... A61B 34/20; A61B 2034/304; A61B 34/30; A61B 90/50; A61B 2090/506;
(Continued)

(56) References Cited

U.S. PATENT DOCUMENTS 5,637,098 A   6/1997   Bierman
5,647,373 A   7/1997   Paltieli
(Continued)

FOREIGN PATENT DOCUMENTS

CN   203280838 U   11/2013
DE   69631481 T2   12/2004
(Continued)

OTHER PUBLICATIONS

International Preliminary Report on Patentability issued in corresponding International Patent Application No. PCT/EP2018/052124 dated Aug. 8, 2019 (10 pages).
(Continued)

*Primary Examiner* — Deanna K Hall
(74) *Attorney, Agent, or Firm* — Kilyk & Bowersox, P.L.L.C.

(57) ABSTRACT

The invention relates to a cannulation robot for the automated affixing of a cannula to a patient. The cannulation robot comprises a fixing apparatus for affixing the cannula to the patient by means of an adhesive carrier. The cannulation
(Continued)

Figure 1:
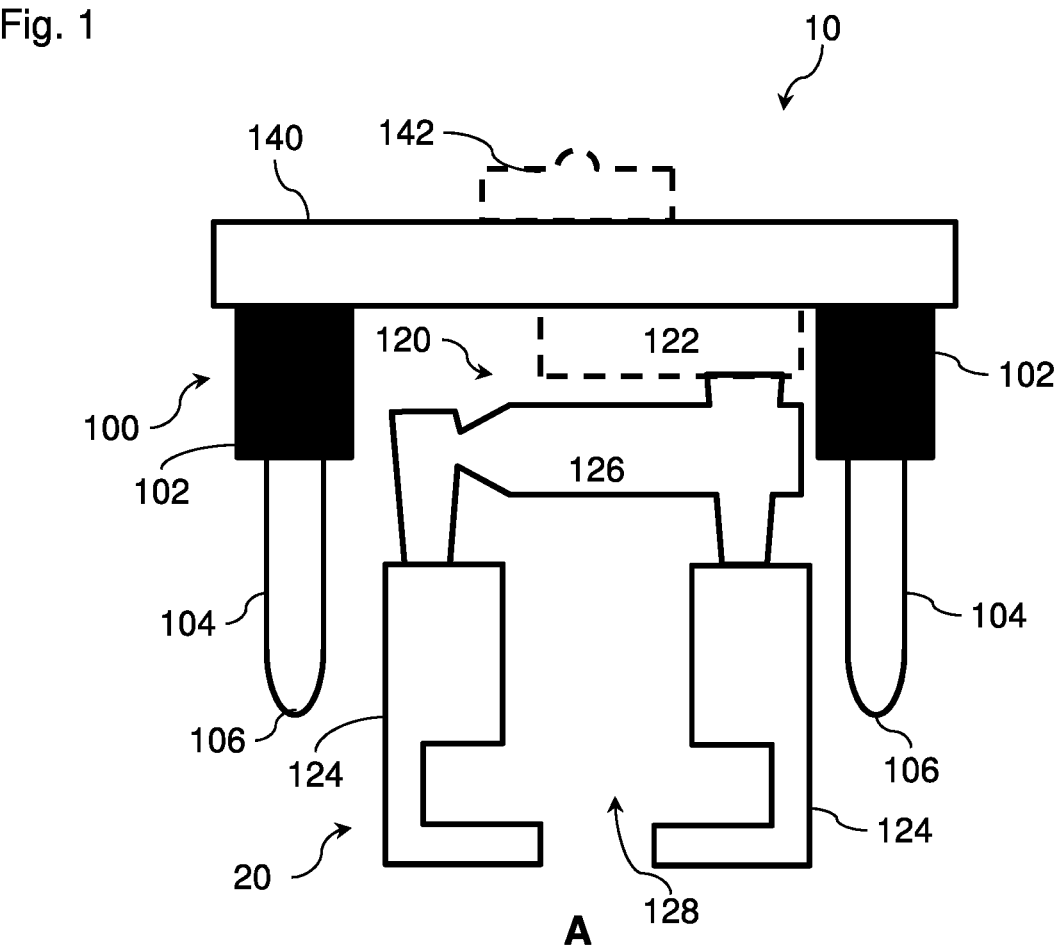
Figure 1:
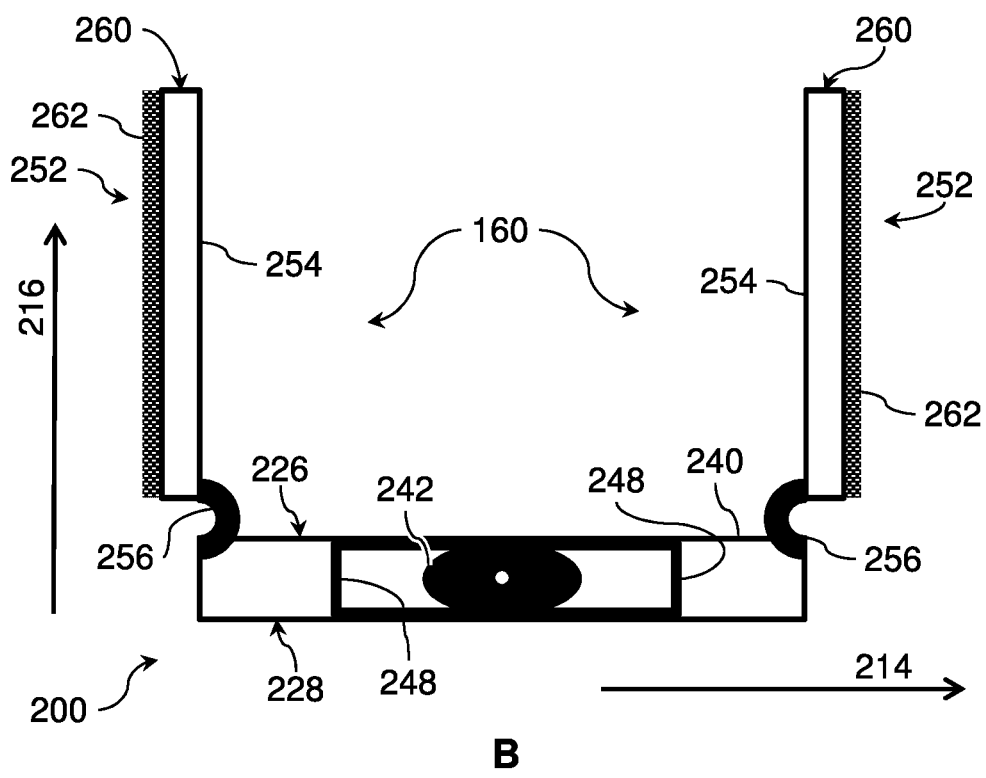

robot comprises a positioning device designed to position a cannula holder of the cannula to an area of the patient's skin. The cannulation robot comprises an actuator device for a guide means, wherein the guide means is designed to guide the adhesive carrier to said skin area. The actuator device is designed to activate the guide means and thereby move the adhesive carrier by means of the guide means toward the skin area, wherein the adhesive carrier contacts the skin area as a result of the movement and adheres to same as well as is disposed such that it is connected to the cannula at least after being adhered.

13 Claims, 5 Drawing Sheets

(51) Int. Cl.
    *A61M 25/02*      (2006.01)
    *A61B 34/20*      (2016.01)
    *A61B 90/50*      (2016.01)
    *B25J 15/00*      (2006.01)
    *A61M 39/02*      (2006.01)

(52) U.S. Cl.
    CPC .......... *A61M 1/3661* (2014.02); *A61M 25/02* (2013.01); *B25J 15/0033* (2013.01); *A61B 2034/301* (2016.02); *A61M 2025/0266* (2013.01); *A61M 2039/0261* (2013.01); *A61M 2205/3553* (2013.01); *A61M 2205/3584* (2013.01); *A61M 2205/3592* (2013.01)

(58) Field of Classification Search
    CPC ... A61B 2034/2059; A61B 2034/2046; A61M 2039/0261; A61M 25/02
    See application file for complete search history.

(56) References Cited

U.S. PATENT DOCUMENTS

| | | | |
|---|---|---|---|
| 2002/0198557 | A1 | 12/2002 | Freigang et al. |
| 2006/0161136 | A1 | 7/2006 | Anderson et al. |
| 2007/0027429 | A1 | 2/2007 | Kuracina et al. |
| 2008/0215035 | A1 | 9/2008 | Yodfat et al. |
| 2008/0275396 | A1 | 11/2008 | Neerken et al. |
| 2009/0069844 | A1 | 3/2009 | Green et al. |
| 2009/0275823 | A1 | 11/2009 | Ayati et al. |
| 2010/0274202 | A1 | 10/2010 | Hyde et al. |
| 2013/0218073 | A1 | 8/2013 | Ekdahl et al. |
| 2015/0065916 | A1 | 3/2015 | Maguire et al. |
| 2016/0249990 | A1 | 9/2016 | Glozman et al. |
| 2016/0249991 | A1* | 9/2016 | Glozman ............... A61B 34/30 606/130 |

FOREIGN PATENT DOCUMENTS

| | | | | |
|---|---|---|---|---|
| DE | 102005032373 | A1 | 12/2006 | |
| EP | 2125077 | * | 4/2018 | ........ A61M 5/14248 |
| JP | 10151197 | A | 6/1998 | |
| JP | 2008522705 | A | 7/2008 | |
| JP | 2010538747 | A | 12/2010 | |
| JP | 2016120313 | A | 7/2016 | |
| JP | 2016538013 | A | 12/2016 | |
| JP | 6234756 | B2 | 11/2017 | |
| WO | 2008078318 | A2 | 7/2008 | |
| WO | 2010056538 | A1 | 5/2010 | |
| WO | 2012088471 | A1 | 6/2012 | |

OTHER PUBLICATIONS

International Search Report and Written Opinion issued in corresponding International Patent Application No. PCT/EP2018/052124 (with English translation of International Search Report) dated May 9, 2018 (16 pages).

Office Action issued in corresponding Chinese Patent Application 201880009320.X dated Apr. 13, 2022 (English translation only)(7 pages).

* cited by examiner

A

B

A

B

AUTOMATIC CANNULATING MACHINE

This application is a National Stage Application of PCT/EP2018/052124, filed Jan. 29, 2018, which claims priority to German Patent Application No. 10 2017 201 434.2, filed Jan. 30, 2017.

The present invention relates to the field of medical technology and in particular to a cannulation robot, a cannula holder and a method for the automated affixing of a cannula.

The puncturing of blood vessels, also known as cannulation, is a routine procedural step in the medical treatment of many patients in which a fluid connection is established between a patient's blood circulation and an external fluid system, in particular a cannula. Cannulation is usually performed by physicians or trained personnel. The quality of the vascular access created by the cannulation thereby depends on a plurality of parameters which are in particular affected by the individual and temporally varying abilities of the medical personnel and the physical characteristics of the patients to be treated as well as the diversity of the technical instruments used in the cannulation. In order to thereby standardize cannulation, make efficient use of financial as well as personnel resources, and reliably ensure high treatment quality, cannulation robots have been developed which autonomously perform a cannulation procedure on patients using suitable sensor technology and motor function. Such cannulation robots and the technical resources thereby used are known from e.g. EP 0 654 244 B1, US 2015/0065916 A1 and WO 2015/052719 A1.

After the blood vessel has been punctured, the cannula, in particular on a cannula holder of the cannula, is normally affixed to an area of the patient's skin in the vicinity of the insertion point by means of an adhesive tape so that the cannula, in particular the part of the cannula penetrating into the blood vessel, remains in the desired position and orientation. Provided that a catheter will subsequently be used for the fluid connection to the patient's bloodstream after the cannula has punctured the blood vessel in the cannulation, the catheter will be accordingly affixed to the patient's skin area, in particular using a cannula holder or catheter holder of the catheter respectively. The cannula, or in particular also the catheter correspondingly, is normally manually affixed by an individual involved in the treatment, in particular by a medical staff member, by the individual involved in the treatment holding the cannula in one hand and affixing an adhesive strip over the cannula, in particular the cannula holder, with the other hand, same extending over a portion of the skin area and thus securing the cannula to said area of the skin.

The observations of cannula and cannulation robot usage which underlies the present invention revealed that fixing the cannula by means of adhesive tape frequently needs to be performed manually and/or that mistakes can frequently occur. In particular, the adhesive tape can thereby curl and as a result in particular adhere to itself or the adhesive tape can adhere to an area not intended for adhesion—for instance to another area of the patient's skin, another medical accessory or to a part of the cannula which the adhesive tape should not adhere to—, the position or orientation of the cannula can undesirably change and/or the cannula or the adhesive strip can become contaminated. The fixation of the cannula thereby impacts the treatment quality, treatment safety and/or the efficiency of resources, in particular in the case of automated cannulation.

The invention is based on the task of, in particular for further developing cannulation automation, automating the affixing of the cannula, increasing reliability when affixing a cannula and/or improving the hygienics.

The invention respectively solves this task by a cannulation robot in accordance with the teaching of independent claim 1, a cannula holder in accordance with the teaching of independent claim 14, and a method for the automated affixing of a cannula according to the teaching of independent claim 15. Preferential embodiments, further developments or variants in particular constitute the subject matter of the independent claims. The subject matter of the claims is expressly made a part of the specification disclosure.

A first aspect of the invention relates to a cannulation robot for the automated affixing of a cannula to the patient in the automated cannulation of a blood vessel of the patient by means of the cannula, in particular for hemodialysis. The cannulation robot comprises a fixing apparatus for affixing the cannula to the patient by means of an adhesive carrier, wherein the cannula is in particular affixed after the cannula has punctured the blood vessel. Additionally, the cannulation robot comprises a positioning device designed to position a cannula holder, which is a component part of the cannula and/or to which the cannula is connected, at an area of the patient's skin at which the cannula is to be affixed. The cannulation robot furthermore comprises an actuator device for guide means, wherein the guide means is designed to guide the adhesive carrier to said skin area. The actuator device is designed to activate the guide means and thereby move the adhesive carrier by means of the guide means toward the skin area, wherein the adhesive carrier contacts the skin area as a result of the movement and adheres to same by means of an adhesive as well as is disposed at least after adhering such that it is in particular directly or indirectly connected to the cannula.

In a broad interpretation, the cannula, the cannula holder, the guide means, the adhesive carrier and/or the adhesive are not component parts of the inventive cannulation robot. Preferably, however, in a narrower interpretation, in particular the guide means, the cannula holder and/or the adhesive carrier can be component parts of the inventive cannulation robot, preferably the fixing apparatus, or at least a preferential embodiment thereof.

In the sense of the invention, a "fixing apparatus for affixing a cannula" is at least to be understood as an apparatus designed to secure a cannula to a patient by means of an adhesive. In particular, the fixing apparatus can realize an affixing procedure; i.e. place an adhesive carrier as well as the adhesive onto an area of the skin in the proximity of the site at which the cannula punctured a blood vessel and by means of same mechanically connect the cannula to the skin area indirectly or directly. In particular, the adhesive of the adhesive carrier can thereby be materially bonded to the skin area and/or to the cannula.

In the sense of the invention, a "cannula" is a tubular body, in particular a rigid or flexible injection needle, with a lumen having a geometry and external dimensions suitable for use in cannulation of a blood vessel. Preferably, the cannula comprises a hollow needle and a connector part. The connector part can in particular be arranged at the proximal end of the cannula and connected, in particular integrally, to the hollow needle so that the cannula can be connected at its proximal end in form-fit or force-fit manner to further apparatus, in particular an infusion tube or a medical syringe, in particular pushed onto same, and the lumen of the cannula fluidly connected to the further apparatus. Preferably, the hollow needle at the distal end of the cannula provided for introduction into a blood vessel is sharp-tipped—in particular with a pointed bevel cut—or blunt.

Preferably, the hollow needle is made from metal and/or the connector part made from plastic. Preferentially, the cannula can also comprise a cannula holder, wherein the cannula, in particular the hollow needle and/or the connector part, can be form-fit or force-fit connected or are preferably integrally connected to the cannula holder.

In the sense of the invention, a "catheter" is a tubular body, in particular a flexible tube, with a lumen having a geometry and external dimensions suitable for being at least partly inserted into a patient's blood vessel and thus establishing a fluid connection between the blood vessel and the lumen of the catheter. In particular, a catheter can be inserted into a blood vessel punctured by a cannula during cannulation; i.e. in particular catheterization. Preferably, the catheter is thereby introduced by means of or together with the cannula or a Seldinger wire initially introduced with the cannula which serves as a guide for the catheter. Preferably, the catheter is designed to be inserted by its distal end into the blood vessel and comprises—preferably at a catheter proximal end opposite from the distal end—a connector part. The connector part in particular enables the catheter to be mechanically connected to the external fluid system, preferably an infusion tube and/or medical apparatus, in particular a hemodialysis machine, thus in particular to be form-fit and/or force-fit—preferably as a plug connection or a screw coupling—as well as the lumen of the catheter to be fluidly connected to the external fluid system. Preferentially, the catheter or at least a part of the catheter provided for introduction into the blood vessel is made from a flexible material and/or the distal end of the catheter is blunt so as to reduce stress and/or irritation of the blood vessel and/or the risk of injury to the blood vessel.

While the invention is described with respect to the affixing of a cannula, it is to be understood that in particular a catheter can, in sofar as technically feasible, likewise be accordingly secured and that the invention also expressly relates to the affixing of a catheter.

In the sense of the invention, a "cannula holder" is at least to be understood as an apparatus by means of which a mechanical connection can be made between a cannula and a gripper apparatus. In particular, a cannula holder is designed to be mechanically connected, in particular integrally, to a cannula on one side and mechanically connected, preferably detachably, to the gripper apparatus on the other side. In particular, the cannula holder can comprise a region, in particular on an underside of the cannula holder, which is coated with an adhesive. Preferably, the cannula holder comprises an adhesive carrier and/or a guide means for guiding an adhesive carrier.

A cannulation robot is an apparatus which automatically; i.e. at least intermittently or continuously, performs at least one cannulation process step in a patient blood vessel, or several or all intended process steps, without the intervention of a human operator, e.g. medical personnel. This thereby ensues in particular by the program parameters of the automated cannulation being accordingly selected by the system and/or by the user. One process step in the cannulation is in particular technically implemented by an apparatus component of the cannulation robot, e.g. a tool device, specifically configured for said process step and is selected from the group comprising the possible process steps P1, P2, P3 . . . , without this numbering defining a sequential ordering:

P1: Using an accessory kit to perform the cannulation which is selected prior to commencing the automated cannulation based on the registered patient identifier; this selection can have been made previously by means of an optional pick-and-place system of the system for selecting an accessory kit and/or equipping an accessory holder, in particular an accessory box; the accessory kit can have been provided beforehand as a function of the registered patient identifier by an optional sorting apparatus of the system selecting the accessories contained in the accessory kit from an optional storage apparatus of the system for storing accessories; the accessory kit can contain one or more medical accessories, in particular gauze, swabs, adhesive tape; the accessories of this accessory kit can be gathered as a function of the registered patient identifier and/or as a function of patient-specific treatment data derived from the registered patient identifier; the use of this accessory kit by the cannulation robot is a process step of the automated cannulation and can provide for the accessories of the accessory kit to be automatically extracted from predetermined positions of an accessory holder/box, in particular by the appropriate program parameters being selected as a function of the registered patient identifier and suitable for extraction; an optional pick-and-place device of the cannulation robot being in particular used to that end which is configured to extract the accessories out of the accessory holder and/or configured to equip one or more optional tool devices of the cannulation robot;

P2: Spatially fixating a part of the patient's body containing the blood vessel, in particular an arteriovenous fistula; the program parameters of the automated cannulation can be selected here as a function of the registered patient identifier, thus individual to each patient, these program parameters setting beforehand the position or the spacing of one or more optional fixation devices of the cannulation robot based on a previously determined location or on predetermined spacings on the patient's body part so as to achieve suitable fixation; the fixation taking place in the treatment chamber of the cannulation robot in which the patient's body part rests for the at least one ensuing cannulation;

P3: Using stored—in particular in a patient database—patient data in order to determine information on past cannulation process steps in the patient's vasculature (historical data), and preferably define the cannulation to occur, in particular the program parameters thereby used, based on this historical data; such historical data containing in particular the location of one or more of the patient's blood vessels previously measured by an optional measuring device of the cannulation robot for measuring the location and/or dimensions of at least one blood vessel under the patient's skin (vascular structure measuring device), and providing same in particular as patient data; such historical data containing in particular information on the location and condition of further puncture sites on the patient's body which is in particular provided as patient data; the vascular structure measuring device being able to be designed to detect the location and/or dimensions of at least one blood vessel under the patient's skin by means of ultrasound or by means of optical radiation;

P4: Identifying the blood vessel under the patient's skin suitable for the blood withdrawal, in particular selecting a suitable insertion site on the skin for the cannulation of said blood vessel; the program parameters of the automated cannulation can hereby be selected as a function of the registered patient identifier, thus individual to the specific patient, by the cannulation planned for the registered patient being selected on the basis of at least one patient-specific treatment parameter; for example with a patient planned for hemodialysis; a treatment parameter can encode the patients necessity for hemodialysis; the cannulation of an arteriovenous blood vessel can be planned by evaluating the treatment parameter; same being identified; the identification can for example ensue in the control system by a program-controlled analysis of an image obtained by a vascular structure measuring device;

P5: Disinfecting the skin of the patient's body part containing the blood vessel; the program parameters of the automated cannulation can hereby be selected as a function of the registered patient identifier, thus individual to the patient, by a disinfecting process being specifically selected for the patient's type of skin or skin morphology which is for example characterized by the length of the treatment or the amount and nature of the disinfecting process employed; treatment data specific to the patient can also be considered; a disinfecting device which is optional with the cannulation robot or separate therefrom and equipped to perform the cited function can be used for the cited disinfection; the type of skin or skin morphology of the patient being preferably known in particular as patient data in the patient database;

P6: Physically treating the patient's body part containing the blood vessel in preparation for the cannulation, in particular stemming the blood flow of the body part, applying pressure to the body part, controlling the temperature of the body part, positioning the immobilized body part; the program parameters of the automated cannulation can hereby be selected as a function of the registered patient identifier, thus individual to the specific patient, by drawing on preparation data specific to the planned patient treatment, e.g. hemodialysis, or which can be taken from the patient database as known preparation data; this preparing for the cannulation of the body part being in particular performed by an optionally provided prepping device of the cannulation robot correspondingly configured for this purpose;

P7: Particularly preferential: Puncturing the blood vessel, in particular an arteriovenous fistula; preferably a first venipuncture and cannulation occurring automatically for withdrawing blood from the blood vessel and a second venipuncture and cannulation occurring automatically for the return of the blood, in particular in the case of hemodialysis; the program parameters of the automated cannulation can hereby be selected as a function of the registered patient identifier, thus individual to the specific patient, by the program parameters defining a patient-dependent motion control for a robotic tool arm optionally provided in the cannulation robot, by means of which a medical accessory such as for instance an injection needle can for example be grasped by the tool arm and positioned on the body part, with the injection needle having been previously selected and prepared specific to the patient; two cannulation robots can be set up for puncturing blood vessels at different parts of the body by, for example, a first cannulation robot being configured for cannulation on an arm and a second cannulation robot being configured for cannulation on a leg; the selection of the appropriate cannulation robot can ensue in patient-specific and/or treatment-specific manner;

P8: Withdrawing blood from the cannulated blood vessel and transporting the blood in at least one blood transport device or in at least one sample container; the program parameters of the automated cannulation can hereby be selected as a function of the registered patient identifier, thus individual to the specific patient, by a suitable blood transport device or suitable sample container being preselected as a function of patient-specific treatment data and then utilized in suitable manner by the cannulation robot; the cannulation robot and the control system can be configured thereto by an appropriate selection of the program parameters to provide at least one sample container based on treatment data for the subsequent, preferably automatic and system-controlled, treatment, in particular diagnostics;

P9: The grasping of a cannula by a gripper apparatus for the cannulation robot(s);

P10: Affixing a cannula by means of a fixing apparatus of the cannulation robot.

The term "cannulation" refers to a procedure in which a cannula is inserted into the blood vessel in the patient's body part by puncturing the skin and venipuncturing the blood vessel wall so that the distal end of the cannula is disposed in the blood vessel and the proximal end of the cannula is disposed on the outside of the body part so that a fluid connection can be established between the cannula and the blood vessel, by means of which fluid, in particular blood and/or fluid media, can be exchanged via the fluid connection. The "exchange" of fluid in this context means that fluid from the patient's blood circulation is conveyed to an extracorporeal fluid system, i.e. situated external of the patient's body, in particular for fluid storage or fluid conduction, and/or includes conveying fluid from the extracorporeal system into the blood circulation. Preferably, subsequent the puncturing, the cannula—or, correspondingly, a catheter after being inserted into the blood vessel—is affixed to the patient, in particular so as to ensure that the fluid connection will be maintained and/or the cannula and/or the catheter does not move relative to the blood vessel and/or the blood vessel is not injured due for instance to movement of the cannula or the catheter respectively.

Chronically ill patients need regularly repeated vasculature cannulation in order to ensure the necessary treatment. One such chronic illness is kidney failure which leads, among other things, to the loss of the blood's natural purifying function. Technical solutions can be substituted in its place. Hemodialysis devices are extracorporeal filtering units serving as artificial kidneys into which the blood of the patent is conducted in order to be cleansed and treated before being returned to the patient's blood circulation. Blood is normally withdrawn and returned via an artificial subcutaneous connection surgically created between a vein and an artery in an arm or a leg of the patient. This connection can be composed of a section of the patient's own vasculature prepared for same or can consist of an artificial material and is referred to as a fistula or arteriovenous fistula respectively (AV fistula, AVF).

The most commonly used permanent vascular access in chronic hemodialysis patients is a native arteriovenous fistula. After the native arteriovenous fistula is placed, it become stronger due to the increased blood flow, whereby repeated cannulation for the dialysis treatment becomes easier.

Hemodialysis must be performed regularly, typically a few days apart. This leads to high mechanical stress on the blood vessel or arteriovenous fistula respectively. Different techniques are known to create access to a blood vessel or arteriovenous fistula respectively, these aiming to be as gentle as possible on the vessel over the course of the repeated cannulation. In rope ladder cannulation, a new cannulation site located at a distance from the previous site, e.g. about 2 cm, is sought for each treatment. In this method, the series of punctures are usually started at the lower end of the vessel and then continue upward until reaching the upper end and the process then started again from below. The practitioner must thereby precisely follow the positioning pattern so as to allow the venipunctured vessel sites to heal. In contrast, in the buttonhole technique, a needle is always inserted into the exact same spot at the exact same angle. Over time, a scar tunnel thus develops which continually displaces the thrombus forming in cannulation and thus becomes more resilient. It has been found that buttonhole technique results can be improved if the cannulation is always performed by the same treatment personnel.

Due to the frequency of cannulation with hemodialysis patients, the arteriovenous fistula is subject in general to high stress, independent of the venipuncture technique, same which can lead to changes in the surface of the skin and the condition of the arteriovenous fistula and how they progress.

One advantage of the cannulation robot can in particular be seen in that, particularly when treating chronic illnesses—in particular with hemodialysis patients—, automated cannulation can reduce the workload of the medical personnel and/or provide a consistently high cannulation precision, whereby in particular treatment quality and/or treatment safety can be increased.

One advantage of the actuator device can in particular be in its working together with the guide means to conduct the adhesive carrier to the skin area, thus in particular move it to the skin area at which the cannula is to be secured. Guiding the adhesive carrier prevents it from adhering to other non-desired areas—for instance the cannula, the adhesive carrier itself or other areas of the patient's skin—and/or lowers the risk that the adhesive carrier loses its form necessary for adhesion—for instance curls up on itself. Moreover, the positioning device enables the cannula holder to be positioned so as to be able to be secured to the skin area by means of the adhesive carrier, whereby the desired position and/or orientation, in particular for post-cannulation treatment, can be ensured.

Compared to manually affixing the cannula, the fixing apparatus in particular has the advantage of being able to further automate the cannulation, since no manual intervention is necessary in the securing process. In particular, the fixing apparatus, which suitably positions the cannula holder and moves the adhesive carrier to the desired area of the skin, enables increasing cannula fixing reliability and thus in particular increasing the treatment safety and/or treatment quality and/or reducing the personnel workload during the cannulation process.

According to one preferential embodiment, the fixing apparatus comprises a segregating apparatus for adhesive carriers. The segregating apparatus has a storage device for adhesive carriers and is designed to sort out an adhesive carrier and thereto extract said adhesive carrier out of the storage device and dispense it at an area near the actuator device. One advantage of the segregating apparatus for the adhesive carrier can in particular lie be in it releasing the adhesive carrier at an area enabling guidance by the guide means, which is actuated by the actuator device, whereby the affixing of the cannula can be further automated. In particular, adhesive carrier storage enables the fixing apparatus to secure the cannula to the patient in automated manner—thus here as well without manually intervening in the supplying or applying.

Preferably, the storage device for adhesive carriers is designed to store a plurality of adhesive carriers, each of a respective predetermined length for an applicable cannula fixation, and to withdraw in each case an adhesive carrier—preferably of suitable length for the respective fixation. This advantageously enables the fixing apparatus to repeatedly and automatically secure cannulas to patients—thus without manually intervening in the supplying of adhesive carriers. Storing adhesive carriers of different predetermined sizes can yield a further advantage of being able in each case to provide an adhesive carrier of suitable length, which can increase in particular the comfort of use.

Preferentially and alternatively or additionally, the storage device is designed to store a longer adhesive carrier, which can be longer than needed for an individual fixation, and to respectively cut off a section from the longer adhesive carrier of a length particularly applicable to the respective fixation. In particular, said longer adhesive carrier can be a roll of adhesive carrier and the storage device can comprise a dispenser device for the adhesive carrier roll as well as the segregating apparatus comprising a cutting device for sectioning off the respective section. One advantage of storing the longer adhesive carrier can in particular lie in it being stored as one physical unit and, particularly when extracting adhesive carriers, or sections of the longer adhesive carrier respectively, being able to handle same as a physical unit. This likewise advantageously enables the specific provision of an adhesive carrier; i.e. sections of the longer adhesive carrier, for a respective cannula fixation.

According to one preferential embodiment, the guide means is a component part of the fixing apparatus and comprises or consists of a transport device, a guide channel and a pressing device. The transport device is thereby designed to gradually or continuously, preferably steadily, transport the adhesive carrier through the guide channel to the pressing device. The actuator device is furthermore designed to move at least the pressing device and the guide channel along the area of the skin to which the cannula is to be affixed. The pressing device is thereby designed to press on that part of the adhesive carrier disposed between the pressing device and that portion of the skin area over which the actuator device is respectively moving the pressing device.

In particular, this movement can delineate a path, in particular a curve, taken on the skin area and/or by the cannula holder and/or by a tube connected to the cannula holder. In particular, the movement—and thus the adhering of the adhesive carrier—can begin or end at the cannula holder and/or at the tube. Preferentially and alternatively, the movement—and thus the affixing of the adhesive carrier—can begin when the cannula holder, or tube respectively, is at a predetermined distance from the skin area. In particular, the movement can also end at a further predetermined distance of the cannula holder, or tube respectively.

Preferably, the distance covered in the movement; i.e. the distance travelled, is synchronized with the transporting of the adhesive carrier, whereby in particular exactly as much adhesive carrier is advantageously sectioned out in each case; i.e. in particular transported out, as will adhere to the skin area during said travel. To that end, the cannulation robot, in particular the fixing apparatus, preferably comprises a distance determination device which virtually captures the respective distance traveled along the skin area and/or the movement of the actuator device and/or the travel of a robotic tool arm of the cannulation robot connected to the actuator device based on a data model of the movement and/or by a sensor technology based on measuring radiation, in particular light, in particular light pulses, ultrasound, electrical resistances and/or electrical capacities, and determines the respective distance travelled therefrom, in particular the length of the path, and stores same in the form of distance data.

As defined by the invention, a "guide channel" is to at least be understood as an apparatus having at least two limiting devices which limit passage through the guide channel on two sides and is configured to guide an object through said passage and by means of the at least two limiting devices. Preferably, the guide channel is closed on at least three sides. In particular, the guide channel can have an inlet opening through which the object to be guided can enter. In particular, the guide channel can have an outlet opening through which the object guided through the passage can exit. In particular, a guide channel can comprise two plates of a sufficiently rigid material as limiting devices, these being adjacently arranged and at a spacing from one another such that a free space is formed between the two plates as the guide channel passage. The two plates thereby limit the maneuvering space of the movement of the object to be guided through the passage. A guide channel in the sense of the invention is in particular a groove, a conduit—in particular of rounded or angular, in particular rectangular, surface area—or a tube stable enough for conduction.

One advantage of guiding the adhesive carrier as well as pressing the respectively selected part of the adhesive carrier can in particular be that those parts of the adhesive carrier which were sorted out—in particular guided out—adhere to respectively corresponding sections of the skin area, while the remaining parts of the adhesive carrier remain stored, transported and/or guided, and thus in particular cannot be erroneously adhered. This advantageously enables increasing particularly the reliability in affixing the cannula.

Preferably, the adhesive carrier comprises a belt conveyor arranged on a side of the remaining part of the adhesive carrier facing the side intended to be adhered to the skin surface by means of the adhesive.

Preferably, the transport device for the adhesive carrier is configured to transport the adhesive carrier by means of the belt conveyor, preferably by the rolling of the belt conveyor. The connection between the belt conveyor and the rest of the adhesive carrier is thereby so pronounced in its strength that the belt conveyor detaches from the rest of the adhesive carrier after the adhering to the skin area due to a lower connecting force between the belt conveyor and the rest of the adhesive carrier compared to the adhesive force on the skin area. One advantage of transporting the adhesive carrier by means of the belt conveyor can in particular lie in the adhesive carrier being able to be conveyed by pulling on the belt conveyor, and/or the strain on the skin area being able to be reduced, since potential tensile strain on the skin area in transporting and/or in supporting the transport by pulling on the belt conveyor can be reduced and preferably prevented. Compared to transport by pushing, a transport by pulling can in particular also have an advantage in that pulling the adhesive carrier pulls in the tensile direction and thus enables preventing divergent motion of the adhesive carrier in an unwanted direction.

According to one preferential embodiment, the fixing apparatus comprises two guide means with transport device, guide channel and pressing device as well as respectively two actuator devices, each activating one of said guide means. This advantageously enables starting the respective movement for placing the respective adhesive carrier at a common starting area, in particular at the cannula holder and/or the tube, whereby the time needed to secure the cannula can be reduced and/or, with movement in the opposite direction, the stress on the skin area and/or the force acting on the cannula can be reduced, as the respective forces of the one guide means counteract the forces of the other guide means.

According to one preferential embodiment, the cannula holder comprises the adhesive carrier, same being arranged on an underside of the cannula holder, which corresponds to an underside of the cannula, and physically connected, in particular materially bonded, force-fit and/or form-fit, to the cannula holder.

Preferably, the adhesive carrier is made from a deformable material—thus in particular comprises same or consists thereof. One such deformable material can in particular be a foam, a rubber or a pasty substance. Preferably, the deformable material, or its ductility respectively, is selected such that the ductility is comparable to the ductility of human skin, whereby the adhesive carrier deforms at least to substantially the same extent as the skin or to a greater extent than the skin when pressed against the skin area. One advantage of the ductility can in particular be enabling a positioning of the cannula and/or cannula holder which is adaptable within the scope of the ductility during the adhering and/or increasing comfort for the patient.

According to one preferential embodiment, the cannulation robot, in particular the positioning device, comprises a robotic tool arm bearing at least one gripper apparatus for grasping the cannula with the cannula holder as a tool device.

Preferably, the positioning device is thereby designed to control the robotic tool arm on the basis of one or more motion control parameters and to position the cannula holder, as grasped by the gripper apparatus, on the skin area via the tool arm. So doing advantageously enables positioning the cannula holder by means of the tool arm and/or by means of the motion of the tool arm.

In particular, the positioning device can be designed as a robotic tool arm having a gripper apparatus. Preferably, the gripper apparatus of the positioning device can thereby be the gripper apparatus of the cannulation robot or, alternatively, the gripper apparatus of the positioning device can be an additional gripper apparatus of the cannulation robot. In particular, these two gripper apparatus can be mounted on the robotic tool arm of the cannulation robot. Alternatively, the cannulation robot and/or the positioning device of the cannulation robot can comprise one respective robotic tool arm each per one each of the two gripper apparatus.

According to one preferential embodiment for a cannula in which its cannula holder has the adhesive carrier on the underside and a robotic tool arm, the actuator device comprises the positioning device. Moreover, the actuator device is designed to move the cannula holder toward the skin area by means of the positioning device and press the adhesive carrier onto the skin area by means of the guide means comprised by the cannula holder or consisting thereof. As a result, the adhesive carrier adheres to the skin area by means of the adhesive and thus establishes a physical, in particular mechanical, connection between the skin area and the cannula holder.

In particular, the cannula holder or a component thereof can serve as the guide means or can cooperate with same to guide the adhesive carrier. To that end, the cannula holder can in particular be designed as the guide means or, respectively, the guide means can in particular comprise the cannula holder configured for the guidance. Alternatively and preferably, the cannula holder and the guide means can be separate components of the cannulation robot, in particular the fixing apparatus, or at least one thereof not being a component of the cannulation robot, wherein both are in particular separate from one another; i.e. the guide means comprises no component part of the cannula holder and, conversely, the cannula holder comprises no component part of the guide means.

One advantage of the combination of cannula holder with the adhesive carrier on the underside and the adhesive carrier being pressed by the robotic tool arm can in particular be that the adhesive carrier's position—and thus particularly also orientation—is dictated by the cannula holder, which represents the guide means, and thus in particular enables preventing adherence to an unwanted location and/or in particular being able to reduce the technical complexity of affixing the cannula.

It is thereby necessary for the gripper apparatus to be configured such that a region on the underside of the cannula holder; i.e. in particular the area at which the adhesive carrier is fixed, remains free in a gripping state of the gripper apparatus and can thus contact the skin In particular, the gripper apparatus can comprise grip regions thereto which are narrower than the cannula holder with respect to the longitudinal axis of the cannula. It is also preferable for the cannula holder to thereby be of large enough dimensions along a longitudinal axis of the cannula and/or along a transverse axis of the cannula as to enable grasping by the gripper apparatus while concurrently keeping a region on the underside of the cannula holder free.

Also an advantage of an enlarged surface at the underside of the cannula holder can in particular be a larger surface for the adhesive carrier and thus a larger adhesive surface and, as a consequence, increased adhesive strength.

Alternatively or additionally, and also preferably, the adhesive carrier can be affixed to a tube, which is attached to the cannula holder in the area of said attachment and to an underside of the tube correspondingly affixed to the underside of the cannula, thereby also enabling embodiments of the gripper apparatus having no free area on the underside of the cannula holder.

Preferably, the cannulation robot, in particular the fixing device, is configured to utilize the affixing of the cannula by means of the adhesive carrier attached to the underside of the cannula holder as a pre-securing; i.e. in particular a pre-fixing, and thereafter undertake additional affixing in accordance with other embodiments. One advantage of the pre-fixing can be in it not being necessary for the cannula to be further held in the desired position, for instance by means of a gripper apparatus and/or the positioning device, during the further fixing. The cannula, in particular the cannula holder and/or the tube, is thereby better accessible to fixing apparatus of further or other embodiments and said fixing apparatus can take up a larger spatial region during the further fixing and/or move through a larger spatial region of the skin area.

According to one preferential embodiment, the fixing apparatus comprises a connecting device for a robotic tool arm. Said connecting device is thereby designed to connect the fixing apparatus to a robotic tool arm, in particular the cannulation robot. One advantage of this connecting device can in particular be in the robotic tool arm being able to be equipped with the fixing apparatus and connected, in particular detachably, thereto.

According to one preferential embodiment with the robotic tool arm, the tool arm is equipped with the gripper apparatus and with the fixing apparatus. In particular, the gripper apparatus and the fixing apparatus can form a common, in particular physical, unit in which the fixing apparatus is arranged adjacent to the gripper apparatus, wherein the gripper apparatus and the fixing apparatus advantageously move in concert, in particular synchronously, by means of the robotic tool arm.

Preferably, the fixing apparatus comprises the actuator device and the guide means, wherein the guide means is arranged adjacent to the actuator device. The fixing apparatus is thereby preferably arranged adjacent to the gripper apparatus, in particular forming a common unit with same, wherein the guide means is also arranged adjacent to the gripper apparatus.

Alternatively and preferentially, the gripper apparatus is designed to dispose the guide means adjacent to the actuator device. In particular, the gripper apparatus and the fixing apparatus can thereby be adjacently arranged and/or the fixing apparatus comprise the actuator device.

Preferably, the gripper apparatus, the robotic tool arm and/or the positioning device are separate components of the cannulation robot.

In particular, however, the gripper apparatus together with the robotic tool arm can alternatively be configured as a positioning device subsequent the puncturing of the blood vessel during cannulation.

Preferably, the positioning device is designed to position the cannula holder at the skin area or at least move it toward the skin area only after the puncturing so as to lessen the angle between an area of the skin around a puncture site, in particular insertion point at which the blood vessel is punctured by means of the cannula, and the cannula, and particularly the cannula and/or cannula holder, contacts the skin area to affix the cannula.

One advantage of the adjacent arrangement of the gripper apparatus and the fixing apparatus can in particular be that after the blood vessel is punctured in the cannulation, the cannula holder can be positioned by means of the gripper apparatus while the fixing apparatus fixes the cannula, whereby in particular no additional apparatus is needed to position the cannula holder during fixation. This advantageously enables in particular reducing the technical complexity and/or increasing reliability since there is in particular no need to change from gripper apparatus engagement to another apparatus.

According to one preferential embodiment, the fixing apparatus comprises a segregating apparatus for adhesive. The fixing apparatus is designed to apply an adhesive onto the adhesive carrier and/or onto the skin area of the patient and/or onto the cannula holder and/or onto a tube connected to the cannula holder by means of the adhesive segregating apparatus. Preferably, the adhesive is thereby a sprayable adhesive, in particular a spray adhesive which is sprayed onto the adhesive carrier or skin area or cannula holder respectively by means of the segregating apparatus for said adhesive. One advantage of applying the adhesive can in particular be that of the adhesive being able to be applied in temporally and/or spatially targeted manner, whereby this can prevent adhesion at an undesired location or at an undesired time and thus in particular enables increasing cannula affixing reliability.

Also preferentially and alternatively or additionally, the adhesive carrier can already exhibit an adhesive, in particular independently of an adhesive being applied by a segregating apparatus. Compared to needing to apply adhesive, this advantageously enables reducing the technical complexity and/or allows providing different adhesive carriers prepared for use, each exhibiting an adhesive respectively adapted to the given adhesive carrier. Together with an additional application of additional adhesive, the adhesive effect is increased and/or different areas/locations—preferably for instance the area of the skin or the cannula holder respectively—provided with adhesive in different ways; i.e. in particular using different adhesives or an adaptable combination of adhesives.

Preferably, the adhesive carrier comprises the adhesive in an activatable form which is initially non-activated; i.e. a form in which the adhesive carrier with said activatable adhesive does not yet adhere.

According to one preferential embodiment for an adhesive carrier having an activatable adhesive, the fixing apparatus comprises an activating device for the activatable adhesive and is designed to activate the adhesive of the adhesive carrier by way of said activating device, in particular at that region of the adhesive carrier which subsequently contacts the area of the skin or the cannula holder or the tube.

In particular, the fixing apparatus can also apply the activatable adhesive to the adhesive carrier by means of a segregating apparatus for adhesive.

Preferably, the activating device for activatable adhesive comprises a light source, wherein a light-activatable adhesive is used. Preferentially and alternatively or additionally, the activating device for activatable adhesive comprises a segregating apparatus for an activating substance, wherein an adhesive which is activatable by means of said activation material is used. Such an adhesive can in particular be a two-component adhesive, whereby one component is the activating substance, an adhesive which requires a chemical catalyst to precipitate its adhesive reaction, wherein the activating substance is the catalyst, or a water-based adhesive which is initially in dry form and dissolves, thus becoming adhesive, upon the addition of water, water being the activating substance in this case.

One advantage of adhesive activation can in particular lie in the adhesive being able to be applied in temporally and/or spatially targeted manner, whereby this can prevent adhesion at an undesired location or at an undesired time and thus in particular enables increasing cannula affixing reliability.

According to one preferential embodiment, the cannula holder comprises a connecting means for connecting to the adhesive carrier. Correspondingly, the adhesive carrier preferably comprises a connecting means for connecting to the cannula holder. In particular, the cannula holder and the adhesive carrier each comprise one respective connecting means, whereby said two connecting means correspond to one another and are configured to physically connect to each another.

In the sense of the invention, connecting means can in particular be adhesives, interlocking engaging elements, magnets, and preferably additionally ferromagnetic materials, screw coupling elements or a welding together.

In the sense of the invention, a physical connection is preferably a mechanical connection. In particular, a physical connection can be materially bonded, form-fit and/or force-fit.

According to one preferential embodiment in which the cannulation robot, in particular the fixing apparatus, is configured for the use of an adhesive carrier and a cannula having a cannula holder comprising at least one connecting means and preferably one respective connecting means for connecting to the respective other, the fixing apparatus comprises the actuator device and the guide means. The fixing apparatus is moreover configured to adhere the adhesive carrier to the skin area and thereby guide it along said skin area via the guide means until, after adhering to said skin area, the adhesive carrier extends over that section of the skin area over which the cannula holder is to be positioned for fixation by means of the positioning device. This advantageously enables the cannula holder and the adhesive carrier to be connected by means of the connecting means or corresponding connecting means respectively, thereby in particular reliably securing the cannula.

Preferably, the fixing apparatus is designed to adhere the adhesive carrier to the area of the skin such that the connecting means of the adhesive carrier, provided same comprises connecting means, is disposed at the skin area section over which the cannula holder is to be positioned for securing. The positioning device is moreover designed to, after the adhesive carrier adheres to the skin area, move the cannula holder to the adhesive carrier and connect them together by means of the connecting means or, provided the cannula holder also comprises connecting means, by means of the corresponding connecting means.

One advantage of connecting the adhesive carrier and the cannula by means of the connecting means or by means of the, in particular at least two, corresponding connecting means, can in particular be that the cannula holder can reliably secure the cannula to the patient's skin area via the connecting means.

Preferably, the adhesive carrier can already be adhered to the skin area at the very start of cannulation; i.e. in particular prior to puncturing the blood vessel. In particular, a control system is to that end designed to designate the puncture site and the desired cannula location; i.e. particularly position and/or orientation, as well as the required positioning of the cannula holder thereto and the skin area for the affixing of the cannula prior to or at least at the start of cannulation—i.e. in particular prior to the adhesive carrier being adhered to the patient's skin area and prior to the blood vessel being punctured. The control system is moreover designed to designate the path over the area of the skin along which the adhesive carrier adheres to said skin area prior to the blood vessel being punctured based on one or more control parameters characterizing said path and control the fixing apparatus and/or a robotic tool arm equipped with the fixing apparatus on the basis of said control parameters such that the fixing apparatus adheres the adhesive carrier to the skin area along said path.

One advantage of the adhesive carrier adhering to the skin area prior to the blood vessel being punctured can in particular be seen in that the cannula can be connected to the adhesive carrier already fixed to the patient after the puncturing, thereby in particular enabling increasing the reliability and/or simplifying the technical realization. An advantage can also be seen in the adhesive carrier being able to support the puncturing of the blood vessel, particularly given a suitably affixed and formed adhesive carrier on the patient—particularly as regards its spatial dimensions, material properties and/or rigidity and/or ductility. Such an adhesive carrier can in this way stabilize in particular the blood vessel and/or the skin in the surrounding area of the blood vessel—particularly by means of its form in the adhered state, its rigidity and/or its resistance to twisting. The inventors in particular capitalize on, particularly compared to manual cannulation, the desired position of the cannula and/or cannula holder already being able to be determined prior to the start of cannulation or at least prior to the puncturing of the blood vessel by means of automation; i.e. in particular by means of the control system.

Preferentially and alternatively, the adhesive carrier or additionally a further adhesive carrier can only be adhered to the skin area after the blood vessel has been punctured—and in particular after the cannula holder has been positioned at the skin area. This advantageously enables being able to react to changes and/or incidents occurring during the puncturing of the blood vessel and/or being able to affix the adhesive carrier such that at least a part of the cannula holder is disposed between the adhesive carrier and the skin area, whereby a particularly stable connection to the cannula holder and/or a particularly reliable securing of the cannula can in particular be realized.

According to one preferential embodiment, the cannula holder comprises at least two fixing elements and a base body. The base body of the cannula holder is thereby connected to the cannula or at least configured to connect to the cannula. The fixing elements are in each case displaceably mounted relative to the base body by respective bearing elements of the cannula holder. Preferably, one or more, in particular all, of the fixing elements are rotatably mounted in terms of rotation about a rotational axis. In particular, different fixing elements can also have different rotational axes. Preferably, when the cannula holder is connected to the cannula, the respective rotational axis points at least substantially in the direction of the longitudinal axis of the cannula or along the transverse axis of the cannula or lies at least substantially in a plane spanned by the longitudinal axis and the transverse axis of the cannula. In particular, one or more of the bearing elements comprises a respective articulated joint, particularly a hinge enabling rotation about the respective rotational axis, or consists respectively thereof. In particular, one or more of the bearing elements is/are configured as a film hinge. Preferably, one or more of the fixing elements is/are configured as wing elements of the cannula holder displaceably mounted on the base body and arranged and mounted such that said wing elements can flip open to fix the cannula or the cannula holder respectively to the skin area.

Preferably, the cannula holder is produced by injection molding and/or made from or consists of plastic. In particular, one or more of the bearing elements can thereby be advantageously produced as a film hinge.

Preferably, one or more of the fixing elements of the cannula holder is/are configured as the adhesive carrier. Said fixing elements are thereby coated with the adhesive and/or at least designed to be coated with the adhesive. In particular, the bearing elements of the cannula holder are thereby configured as the guide means, whereby in each case they guide a respective one of the fixing elements, in particular with a rotational motion, toward the skin area.

Preferentially and alternatively or additionally for an additional adhesive carrier, one or more of the fixing elements comprises a connecting means for the adhesive carrier or the additional adhesive carrier respectively. In particular, also the base body of the cannula holder can comprise such connecting means. This advantageously enables the connecting elements to connect the adhesive carrier, or the additional adhesive carrier respectively, to the cannula holder during the producing or preparing of the cannula holder for affixing the cannula or during cannulation, in particular when securing the cannula. In particular, the cannula holder comprises the adhesive carrier and is connected to same by means of the connecting means; or alternatively, the cannula holder does not comprise the adhesive carrier or the additional adhesive carrier respectively and is designed to connect to said adhesive carrier by means of the connecting means.

Preferably, one or more of the fixing elements of the cannula holder, particularly in the case of a cannula holder having a connecting means, comprises a respective cavity to be arranged alongside the respective fixing element and on the side on which the adhesive carrier is disposed, or to be connected by means of connecting means of the cannula holder which extend to the opposite side such that the adhesive carrier or at least a part thereof remains accessible through said cavity when the adhesive carrier and the respective fixing element rest on the skin area. One advantage of this cavity can in particular be the adhesive carrier being able to be pressed against the patient's skin area through said cavity, for instance by means of a pressing device.

According to one preferential embodiment, the cannulation robot, in particular the fixing apparatus, is configured to use a cannula holder comprising the guide means, which has at least two fixing elements and a respective bearing element for each respective fixing element as the guide means, to secure the cannula to the patient. To this end, the actuator device comprises one or more pressure rods, each allocated to one or more of the fixing elements, as well as an actuator for the pressure rods. The actuator device is additionally designed to actuate the pressure rods by means of the actuator and in each case move a distal end of a respective pressure rod to a respectively associated fixing element and respectively press the fixing element toward the skin area via the pressure rod, in particular until the adhesive carrier disposed with the fixing elements touches the skin area.

According to one preferential embodiment, the actuator of the actuator device is mechanically connected to a connecting device for a robotic tool arm. In addition, the connecting device can be arranged in a predetermined manner relative to the positioning device and the cannula holder positioned by means of the positioning device and/or can be arranged by means of the robot-controlled tool arm such that the pressure rods of the actuating device are or can be arranged with the cannula holder—in particular its fixing elements—and can press against same to actuate the fixing elements. In particular, a control system of the cannulation robot can additionally determine one or more control parameters for the movement of the robotic tool arm to a predetermined position relative to the positioning device and/or the cannula holder and control the robotic tool arm based on said control parameters such that it travels to the predetermined position.

According to one preferential embodiment, the cannulation robot, in particular the fixing apparatus, is configured to utilize a cannula holder comprising a base body and in which the fixing elements are designed as wing elements rotatably mounted about a rotational axis relative to the base body by means of the respective bearing element, wherein their wing tips in particular point away from the skin area in an initial state prior to affixing the cannula. The actuator device is designed to first move, by means of the actuator, the distal ends of the pressure rods toward the base body or toward a respectively associated wing element or its bearing element and upon encountering a mechanical resistance, particularly the base body or the respectively associated wing element or its bearing element respectively, effect a spreading motion by which the distal ends of the pressure rods are in each case moved outwardly away along the associated wing element from the base body. This advantageously enables the wing elements to flip open away from the base body in the direction of the skin area.

Preferably, the pressure rods in each case comprise a pressing device, in particular a roller, at their distal ends which presses the adhesive carrier against the skin area. The pressing of the adhesive carrier preferably ensues by means of the fixing elements, same being allocated to a respective one of the pressure rods. Alternatively and preferentially, the adhesive carrier is pressed through cavities of the fixing elements, wherein the pressing devices press directly on the adhesive carrier in each case. In particular, the pressure rods can also move the respective fixing elements toward the skin area by pressure on a respective part of the adhesive carrier accessible through the cavity.

According to one preferential embodiment, the actuator device has two pressure rods rotatably mounted about a rotational axis relative to a supporting element by means of an articulated joint. The supporting element is movable along an axis, in particular an axis facing the cannula holder, by means of an actuator. The pressure rods comprise in each case a distal and a proximal end, wherein the distal ends are arranged away from the supporting element and the pressure rods point away from the supporting element toward its distal ends. In particular, the pressure rods are thereby in each case rotatably mounted at their proximal end on the supporting element. Upon the supporting element moving along a first axis direction, the pressure rods, and thereby the distal ends of the pressure rods, initially move in the same direction as the supporting element until the distal ends of the pressure rods encounter a mechanical resistance, in particular of the cannula holder. Encountering the mechanical resistance leads to the further movement of the supporting element resulting in a rotational movement of the pressure rods relative to the supporting element due to the rotatable mounting of the pressure rods. The pressure rods thereby define in particular a spreading motion, with which the distal ends of the pressure rods are moved outwardly away.

Preferably, the actuator device and/or the pressure rods comprise, particularly in each case, a restoring element, in particular a spring, which effects a rotational force which acts against the rotational motion induced by the movement of the supporting element along the first axis direction.

This advantageously enables fixing a cannula holder with wing elements, in particular lateral wing elements, to the patient by the respective distal ends of the pressure rods opening a wing element in the direction of the patient's skin area after it comes into contact with the respective wing element or the base body in the first direction movement along the axis, whereby the base body or the respective wing element acts as mechanical resistance.

According to one preferential embodiment having a storage device for adhesive carriers, said storage device is designed to store at least two different adhesive carriers. Alternatively or additionally and preferentially, this embodiment can also comprise a segregating apparatus for adhesive designed to sort out at least two different adhesives.

The cannulation robot, in particular the fixing apparatus, comprises a detection system for tissue and/or skin types, which detects data on the nature of an area of the skin and preferably the tissue underneath, in particular the blood vessel, by means of sensor-based measuring of radiation, in particular light, mechanical forces and/or chemical substances and stores same in the form of tissue and/or skin type identifying data. Said detection system can in particular comprise or consist of an image recognition system, wherein the image recognition system has one or more cameras in order to obtain data on skin type by capturing one or more images.

The cannulation robot is furthermore designed to implement a selection process. To this end, the cannulation robot can in particular comprise a control system or be connected to such a control system designed to implement the selection process. The selection process comprises the following steps. In one procedural step of the selection process, data is gathered by means of the tissue/skin type detection system on the nature of the skin and preferably the tissue underneath for the area of the patient's skin at which the cannula is to be affixed. In one procedural step of the selection process, the tissue and/or skin type of the skin area is determined based on the detected identifying data using a tissue/skin type database. In one procedural step of the selection process, an adhesive carrier is selected from among the stored adhesive carriers and/or an adhesive from among the adhesives which is suitable for the specific tissue type and/or skin type based on the database or a further database. In one procedural step of the selection process, one or more control parameters characterizing the selected adhesive carrier and/or selected adhesive are output for at least one of the segregating apparatus.

Lastly, at least said segregating apparatus of the cannulation robot, in particular the fixing apparatus, is designed to be controlled by the cannulation robot, in particular the fixing apparatus, or the control system on the basis of said control parameters and separate out the adhesive carrier and/or the adhesive characterized by said control parameters.

One advantage of the selection and segregating of a suitable adhesive carrier and/or adhesive can in particular be that the securing of the cannula is made more reliable and/or problems during affixing—for instance allergies, insufficient adhesiveness or excessive adhesiveness, which complicates the later removal of the adhesive carrier—can be prevented and thus in particular enables the comfort of use and/or treatment safety to be increased.

Preferably, for instance in a case of the skin being damp, an adhesive can be used, in particular selected, which is insoluble in water or at least poorly soluble in water and thus also realizes sufficient adhesive force on damp skin, and/or an adhesive carrier used, in particular selected, which enables moisture removal—for instance through the pores.

An adhesive carrier which has a flexible surface or structure and/or profile on its adhesive side can also be used, in particular selected, for instance preferably with a hairy area of skin, wherein clear skin areas can be reached through the hair growth, and/or an adhesive used, in particular selected, which can be loosened particularly well from hair—for instance a water-soluble adhesive or an adhesive with reduced adhesiveness to hair.

An adhesive carrier can for instance preferably also be used, in particular selected, in a color which at least substantially matches the skin color of the patient.

According to one preferential embodiment, the cannulation robot, in particular the fixing apparatus, comprises a detection system for cannula location, which detects data on the cannula location, in particular in a blood vessel, by means of sensor-based measuring of radiation, in particular light, mechanical forces and/or ultrasound and stores same in the form of cannula location identifying data. The cannulation robot, in particular the fixing apparatus, is thereby designed to move the cannula, particularly at a predetermined and preferably minimal displacement and/or force, by means of the positioning device after the cannula has been affixed. The detection system is designed to detect the change in location of the cannula, in particular in the punctured blood vessel of the patient, upon the movement. Lastly, the cannulation robot, in particular the fixing apparatus and/or a control system, is designed to determine whether the cannula is sufficiently secured based on the detected movement of the cannula.

One advantage of checking the fixing of the cannula via a movement can in particular lie in the movement corresponding to an actual situation—in which for instance the cannula or a tube affixed thereto is mechanically stressed—and thus the result of this verification being particularly reliable, particularly compared to a passive check without cannula movement, whereby in particular treatment safety can be increased. One advantage of the predetermined and minimal displacement during the movement and/or the predetermined and minimal force can in particular be being able to prevent the secured cannula from detaching due to excessive movement or force respectively. In particular, the displacement and/or the force can be prespecified such that, on the one hand, a realistic force for actual load situations which can occur prior to, during or after a patient treatment acts on the affixed cannula and, on the other hand, the force is still so low that there is no degrading of the fixation or even an undoing of the fixation—particularly given initially proper fixation.

According to one preferential embodiment, the cannulation robot comprises a control system or is data-linked to a control system.

The control system is preferably designed to control or implement respectively the cannulation robot and/or at least some of its components and/or functions. In particular, the control system is designed to control a robotic tool arm of the cannulation robot on the basis of control parameters. In particular, the control system is designed to implement a selection procedure for selecting an adhesive carrier and/or an adhesive and/or a segregating apparatus of the cannulation robot, in particular the fixing apparatus, for sorting out the selected adhesive carrier and/or selected adhesive. In particular, the control system is designed to control a gripper apparatus, a fixing apparatus, an actuator apparatus and/or a positioning device of the cannulation robot. This advantageously enables one or more functions of the cannulation robot to be automated and/or subject to program-controlled execution.

Preferably, the control system is also designed to receive and process data from at least the cannulation robot, in particular from some of the components of the cannulation robot, in particular also control said components, in order to prompt them to output corresponding data to the control system—i.e. in particular transmit—and/or to in turn control the cannulation robot or its components on the basis of the received data and/or the results of processing said data. In particular, the control system is designed to control a detection system for cannula location and/or a detection system for tissue and/or skin type and/or receive data thereof. The cannulation robot can thus advantageously interact with its environment and/or its components. This thereby in particular enables realizing a regulation—preferably for instance of a robotic tool arm of the cannulation robot.

The invention also expressly relates to a fixing apparatus for affixing a cannula to a patient.

Preferably, the fixing apparatus comprises the positioning device, the actuator device, the gripper apparatus and/or the connecting device for a robotic tool arm. Preferentially and additionally or alternatively, the fixing apparatus can also exhibit a robotic tool arm, whereby same can in particular comprise a connecting device for a cannulation robot. Furthermore, the fixing apparatus can comprise a detection system for cannula location, a detection system for tissue and/or skin type, a segregating apparatus for adhesive carriers, a segregating apparatus for adhesives, a segregating apparatus for cannula holders and/or cannulas, one or more adhesive carriers, one or more adhesives, one or more cannula holders, one or more cannulas, in particular with respective cannula holders, and/or the guide means. It is thereby obvious that these can also not be respective component parts of the fixing apparatus.

The previously cited possible advantages as well as embodiments, further developments or variants with regard to a fixing apparatus of the cannulation robot also apply correspondingly to the inventive fixing apparatus.

A second aspect of the invention relates to a cannula holder, in particular for a fixing apparatus and/or a cannulation robot according to the first aspect of the invention. The cannula holder comprises a base body as well as one or more regions for affixing the cannula holder to a patient. The base body is connected to the cannula and/or designed to be connected to a cannula. The regions of the cannula holder are connected to one or more adhesive carriers or designed to be connected to same.

The previously cited possible advantages as well as embodiments, further developments or variants of the first aspect of the invention also apply correspondingly to the inventive cannula holder. Inversely, the following cited possible advantages as well as embodiments, further developments or variants of a cannula holder according to an embodiment of the second aspect of the invention also apply correspondingly to a fixing apparatus and/or a cannulation robot according to an embodiment of the first aspect of the invention having or respectively for a cannula having such a cannula holder.

In particular, the cannula can be a component part of the cannula holder or, inversely, the cannula holder can be a component part of the cannula which in particular also comprises a hollow needle for puncturing a blood vessel of the patient.

Preferably, the cannula holder, in particular the base body, has a connecting area for particularly integrally connecting to the cannula or to the hollow needle.

According to one preferential embodiment, the cannula holder is made of a disinfectable material. Preferably, the cannula holder is made from a plastic. Also preferably, the cannula holder is already connected to a cannula in the manufacturing process and both disinfected together and thereafter packaged. This advantageously enables improving the hygienics and/or increasing the treatment quality or treatment safety.

According to one preferential embodiment, the regions on the base body for securing the cannula holder are arranged and the base body, in particular the connecting area of the base body, designed such that the regions for securing the cannula holder are spaced from the cannula, in particular the hollow needle of the cannula. One advantage of this spacing can in particular be in being able to prevent contaminants during cannula affixing and in particular being able to secure the hollow needle of the cannula to the patient by means of the cannula holder, whereby treatment safety in particular can be increased and/or stressing of the puncture site can be reduced.

A third aspect of the invention relates to a method for the automated affixing of a cannula to the patient in the automated cannulation of a patient's blood vessel by means of the cannula, in particular for hemodialysis. In particular, a cannulation robot in accordance with the first aspect of the invention can be operated by way of the method and/or a cannulation robot according to the second aspect of the invention can be used in the method. The method comprises the following procedural steps. In one method step, a cannula with a cannula holder is provided or a cannula without a cannula holder is first connected to a cannula holder and then provided. In one method step, a guide means is actuated by means of an actuator device, whereby the guide means leads an adhesive carrier to an area of the patient's skin at which the cannula is to be affixed. In one method step, the cannula holder is positioned at the skin area by means of a positioning device. In one method step, the cannula is affixed to the skin area by means of the cannula holder and the adhesive carrier, in particular after the blood vessel has been punctured by said cannula, whereby the adhesive carrier is adhered to the skin area by an adhesive and connected to the cannula.

The previously cited possible advantages as well as embodiments, further developments or variants of the preceding aspects of the invention also apply correspondingly to the inventive method for automated cannula affixing. Inversely, possible advantages as well as embodiments, further developments or variants of the method according to the third aspect of the invention also apply correspondingly to the preceding aspects of the invention.

In particular, the provision of the respective means—in particular the cannulation robot, the adhesive carrier, the adhesive and/or the cannula holder—can in each case constitute one part of the method; i.e. in particular a method step, or alternatively one or more of said means can also be provided prior to implementing the method.

According to one preferential embodiment, a tube, in particular an infusion tube, is automatically fluidly connected to a connector part of the cannula prior to, during or after the cannulation; i.e. in particular the puncturing of the blood vessel and/or the affixing of the cannula.

One advantage of connecting while the cannula holder is engaged with a gripper apparatus or the cannula holder is being positioned by means of the positioning device can in particular be in being able to reduce the mechanical stressing of the cannulated blood vessel.

One advantage of connecting prior to the cannulation or at least prior to the puncturing of the blood vessel can in particular lie in not needing to prevent blood leakage through the connector part and the connecting thereby being made easier and/or the cannula not needing to comprise any additional device such as a valve or control lever to prevent blood leakage.

One advantage of connecting after the cannulation or at least after the affixing of the cannula can in particular lie in the fixation being able to ensure the location of the cannula and/or apparatus not needing to take hold of the cannula or its cannula holder in order to determine its location and thus such apparatus, for instance the gripper apparatus and/or the positioning device, can already be separated from the cannula or its cannula holder respectively when connecting to the tube, whereby in particular collisions between different apparatus for holding or securing the cannula and for connecting the tube to the cannula can be avoided.

Preferably, the cannula holder comprises a connector part designed for fluid connection with a tube. In particular, said connector part of the cannula holder can be the cannula connector part for the tube.

The invention also expressly relates to a system for the treatment and in particular the cannulation of a patient. Said system comprises a cannulation robot for the automated cannulation of a patient's blood vessel and thereby a fixing apparatus for affixing the cannula to the patient, in particular in accordance with the first aspect of the invention, one or more cannulas, as well as one or more cannula holders, in particular in accordance with the second aspect of the invention, and a control system. Preferably the cannulas are in each case integrally connected to one of the cannula holders. The system also preferably comprises at least one storage area for cannulas, in particular cannulas with cannula holders. Preferably, the system is designed to realize a method in accordance with the third aspect of the invention. In particular, the cannulation robot can comprise a robotic tool arm to that end, same being equipped with the fixing apparatus and/or a gripper apparatus, and which extracts a cannula with cannula holder from the storage area by means of said tool arm—thus in particular grasps same by the gripper apparatus—and/or affixes the cannula to the patient via the fixing apparatus after the blood vessel has been punctured.

To be understood by the upper side of the cannula is, in terms of cannula partitioning, that side of the cannula along a plane in which a longitudinal axis of the cannula faces away from the patient when the distal end of the cannula is inserted into the patient; i.e. in particular during or after cannulation. Correspondingly, the other side; i.e. the side facing the patient, is the underside of the cannula.

A cannula usually exhibits a distal and a proximal end. A longitudinal axis of the cannula thereby extends from the proximal to the distal end of the cannula and usually along a hollow needle of the cannula. Preferably, a cannula holder is connected or connectable to the cannula, in particular integrally, in the region of the proximal end.

In the connected state and/or in the case of the cannula holder being a component part of the cannula or, inversely, the cannula being a component part of the cannula holder, the upper side of the cannula and the upper side of the cannula holder as well as the underside of the cannula and the underside of the cannula holder in particular correspond to one another.

A vertical axis of a cannula or a cannula holder extends in particular from the underside to the upper side.

A cannula usually has two longitudinal sides, a first longitudinal side and a second longitudinal side. The longitudinal sides are defined by a plane of the cannula which runs between the distal and the proximal end of the cannula and/or with the longitudinal axis enclosing an angle of no more than 45°, preferably at most 15°, preferably at most 5°, and further preferentially 0°, and situated on the one or respectively other side of the plane. This plane also runs from the upper side of the cannula to the underside of the cannula and encloses an angle between 45° and 135°, preferably between 70° and 110° and preferably between 85° and 95°, particularly with an area which separates an upper region above the upper side of the cannula from a lower region below the underside of the cannula, and is preferably at least substantially orthogonal to this area.

In the sense of the invention, a "transverse axis" of the cannula is at least to be understood as an axis which extends from a first of the cannula's longitudinal sides to a second of the cannula's longitudinal sides.

In the sense of the invention, an "adhesive carrier" is at least to be understood as a supporting material for adhesive. Preferably, the adhesive carrier is of strip-like supporting material for adhesive or comprises same. Such supporting material can in particular be plastic films, foams, in particular of plastic, plant tissue, paper, metal films, textile fabric or a combination thereof. Preferably, the adhesive carrier is coated on at least one side—the adhesive side—with adhesive. Preferentially and alternatively or additionally, the adhesive carrier can be designed to be coated with an adhesive on the adhesive side. An adhesive carrier which is already coated with an adhesive is also referred to as a self-adhesive adhesive carrier. The adhesive carrier can also have further adhesive sides. In particular, the adhesive carrier can have a respective adhesive side on two opposite sides—thus being a double-sided adhesive carrier.

Preferably, the adhesive carrier is flexible enough to be adhered to particularly a non-planar region of a patient's skin—for instance the skin of a patient's arm—without at least substantially deforming the skin and/or the underlying tissue. Preferably, the adhesive carrier, the adhesive and the skin area act together such that a cannula affixed to the skin area by means of the adhesive carrier will not be dislodged under the common stresses to be expected on the cannula. Preferably, the adhesive carrier is tear-resistant enough such that after being adhered to a patient's skin area, it will not tear under normal load, in particular at a connecting point with the cannula holder, and/or can be pulled off from the skin area to remove said adhesive carrier and thereby overcome the adhesive force of the adhesive relative the skin and/or relative the adhesive.

Adhesive carriers in the sense of the invention are in particular an adhesive plaster, an adhesive tape—in particular a medical adhesive tape—, an acrylate foam adhesive tape, a double-sided adhesive tape, a medical bandage, a strip-like cloth, a gauze bandage or a combination thereof.

In the sense of the invention, an "actuator" is at least to be understood as a controllable drive apparatus for mechanically moving and/or displacing an object. Such an actuator is thereby preferably designed to be controlled on the basis of a signal and convert this signal into a motion. Preferably, an actuator comprises one or more drive apparatus. In particular, an actuator can be an electric actuator and be electrically controlled. To that end, such an electric actuator preferably comprises one or more electric motors as drive apparatus. Preferably, the actuator comprises a gearing configured to convert a motion of at least one of the drive apparatus into the mechanical movement for moving and/or displacing objects. In particular, such a gearing can be designed to convert a rotary motion into a translational motion. Furthermore, the actuator can comprise sensor technology based on measuring radiation—in particular light—, mechanical forces, electrical resistances, electrical capacities, electrical interactions and/or mechanical pressures, in particular in order to determine the position reached in each case with the mechanical movement and/or displacing of the object.

In the sense of the invention, a "gripper apparatus" is at least to be understood as an apparatus designed to mechanically grasp an object. In particular, the gripper apparatus can realize a gripping action; i.e. grabbing the object, and thereby make an indirect or direct mechanical connection with the object. Preferably, the connection is detachable, the grasped object can thus be released.

In particular, the gripper apparatus is designed for a cannulation robot and for grasping a cannula with a cannula holder. The gripper apparatus comprises two gripper elements and a moving device. The two gripper elements are movable relative to each other and work in concert to grasp the cannula holder. The moving device is configured to move the two gripper elements relative to each other and to move at least one of the gripper elements relative to the cannula holder. The gripper apparatus can thereby be brought into a gripping state in which at least one of the gripper elements engages with the cannula holder.

As defined by the invention, "configured" refers to an apparatus not only being in principle suited to fulfill a specific function—for instance only after a specific program code has been loaded; i.e. the apparatus programmed, or the apparatus formed in a specific way—but the apparatus already possesses all the means necessary in order to actually fulfill the function. Preferably, the apparatus is to that end already programmed with a program code for said function and/or already configured and/or arranged and/or exhibits such a configuration thereto that the apparatus actually fulfills the function.

As defined by the invention, "on the basis of" is at least to be understood as "due to" and/or "as a function of." In particular, the one or more parameters to be determined can be determined on the basis of a characteristic value, an input variable or one or more of the preceding parameters or a combination thereof. The result, i.e. the specific parameters, can thereby depend on part of the basis on which the determination is based—in particular functional, particularly linear or polynomial—while not depending on another part of the basis. The dependency can also be contingent on a part of the basis; i.e. in particular the part of the basis determining on which parts of the basis the result depends. The same applies accordingly to the control or actuation, in particular based on parameters, characteristic values or input variables.

"Treatment of a patient" in the sense of the invention refers to at least one medical; i.e. in particular therapeutic, diagnostic or cosmetic, procedure which effects changes to the body and/or health of the patient or by means of which the state of the patient's health is determined. A treatment is in particular an administration of medicinal products, a cannulation, a blood purification procedure such as dialysis, an operation and/or an examination of the patient.

A "group of treatments" in the sense of the invention can be respective specific operations, therapy for a specific illness, the initial examination of a patient, or a dialysis treatment which in turn can comprise sub-groups, in particular hemodialysis, hemofiltration, hemodiafiltration, hemoperfusion or peritoneal dialysis treatments. Apheresis constitutes a further possible treatment group.

As defined by the invention, an "individual involved in the treatment" can in particular be understood as an attending person, for instance a physician, or an individual providing treatment support, for instance a nurse. In particular, the patient to be treated can himself also be an individual involved in the treatment or an attending person.

To be understood by a "data processing apparatus" in the sense of the invention is at least one apparatus configured to process data; i.e. in particular to receive data, store received data, read out stored data, transform received and/or stored and/or read data by means of logical and/or mathematical operations, store transformed data, and/or output transformed and/or read data. Preferably, such a data processing device is programmable; i.e. a program code in particular at least partially specifies the method for processing the data and at least part of said program code is modifiable.

Preferably, the data processing apparatus is a commercially available computer. Further preferentially, the data processing apparatus comprises at least one data processor—i.e. a central processing unit—, in particular a microprocessor, a non-volatile—i.e. in particular permanent—data storage, in particular a hard disk, a read-only memory (ROM) or a drive with a data medium, as well as at least one hardware interface. The data processing apparatus also preferably comprises a volatile electrical data storage, in particular as main memory, preferably a semiconductor memory, in particular with integrated capacitors and/or flip-flops (bistable multivibrators) for data storage, for instance dynamic RAM or static RAM.

In the sense of the invention, a "data storage apparatus" is an apparatus for storing data. Same is in particular designed to form a data link with a further apparatus, particularly a data processing apparatus, and/or comprises a data link to the further apparatus, wherein data can be transmitted to the data storage apparatus from the further apparatus for storage by means of the data link and/or data can be transmitted from the data storage apparatus to the further apparatus for retrieval. Preferably, the data storage apparatus comprises at least one mon-volatile data storage. Also preferably, the data storage apparatus comprises at least one volatile electrical data storage.

A communication device is preferably configured to transmit and/or receive data, in particular for data exchange over a data link provided by the communication device, particularly for a remote data link to a remote device. The data link, in particular remote data link, can be established by a restricted (in particular intranet) or global network of computers (in particular a WAN and/or the internet). The data link, in particular remote data link, can also be established by wireless connection, in particular radio link. The data link, in particular remote data link, can in particular be established by mobile radio connection.

A data link connects in particular two data processing units, in particular two data processing devices or apparatus, in a way so as to enable the exchange of data between the units, either unidirectionally or bidirectionally. The data link can be realized in wired or wireless manner, in particular as a radio link. A remote data connection connects in particular two data processing units, particularly two data processing devices, disposed at a distance from one another, thus not being component parts of the same device, in particular the same user interface device or the same control system, if the cited devices are realized as separate units. A data link, in particular remote data link, of one device to another device is preferably realized by a direct connection between the two devices or by an indirect connection of the two devices such that a third device is connected between the two devices in order to pass on the data. A remote data link can in particular be realized by a network of computers with which the devices connected by the remote data link are interconnected via the network. The network can be a restricted network, e.g. an intranet, or global network, in particular a WAN and/or the internet.

In the sense of the invention, an "interface device" serves the connection of two units—in particular including systems, apparatus, devices or mechanisms, particularly having such units—, respectively capable of processing signals, in particular information, particularly data, thus in particular sending and/or receiving. An interface device can comprise at least one hardware interface and in particular be integrated into a physical device unit as a component part.

In the sense of the invention, a "control system" is a system which comprises a data processing apparatus and/or a volatile or permanent data storage, in particular a data storage apparatus, and is designed to control a system comprising the control system, in particular the mobile selection system, its components and/or one or more apparatus external of the system; i.e. in particular also further systems or mechanisms, preferably for instance a cannulation robot or a robotic tool arm or a gripper apparatus or a fixing apparatus or a segregating apparatus. The control system is preferably designed to implement the selection process and/or a control procedure particularly by means of a program code suitably constructed for the purpose and executable by a data processing apparatus.

The control system can be formed by an individual control apparatus. Preferably, the control system comprises a plurality of control devices which can be independent apparatus or the components of other apparatus of the system. In particular, some or all of said control devices can be organized into a network for data exchange. In the case of a user interface having its own control device and/or the cannulation robot having its own control device, said control devices can be regarded as component parts of the control system. It is however also possible for the control system to not exhibit these optionally provided control devices.

In particular, the control system can even also be integrated into one physical unit together with the cannulation robot and/or the fixing apparatus.

The control system, a user interface of the control system, the detection system, the fixing apparatus or component parts of these components can also be at least partly implemented by software functions or can in particular partly implement program code.

In the sense of the invention, "control," in particular control provided by a control system, ensues on the basis of a characteristic value, an input variable, one or more parameters or a combination thereof. The control can also include regulation. Thus, a control system can for instance control a robotic tool arm on the basis of control parameters governing a movement such that a part of same, and particularly a tool—preferably a gripper apparatus and/or a fixing apparatus—is moved pursuant to said control parameter. The movement can thereby be detected by sensor technology, in particular the robotic tool arm, and the control parameters can be adapted in a control loop using the detected movement.

Further advantages, features and possible applications of the present invention are yielded by the following detailed description of at least one example embodiment and/or by the figures. Unless otherwise described or contextually indicated otherwise, the same reference numerals are substantially used to identify equivalent components in the embodiments.

Figure 2:
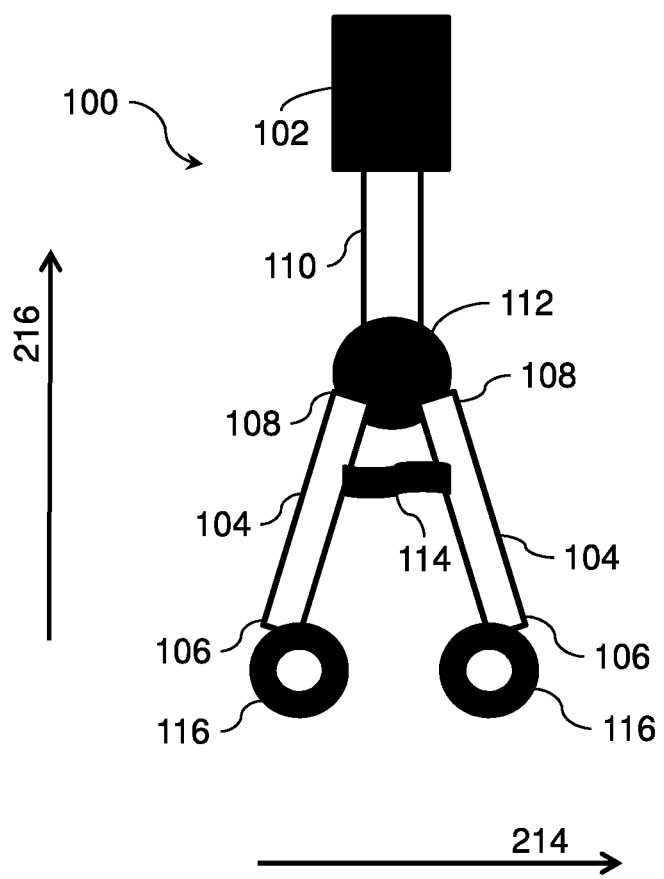
Figure 3:
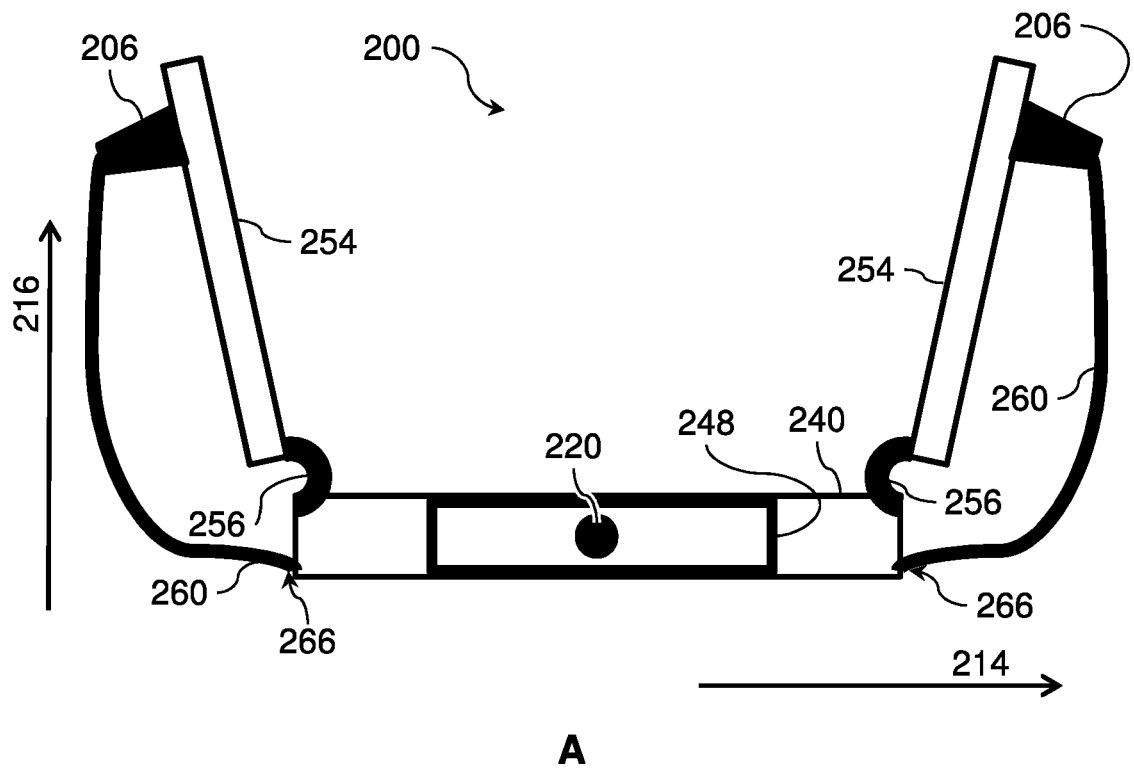
Figure 3:
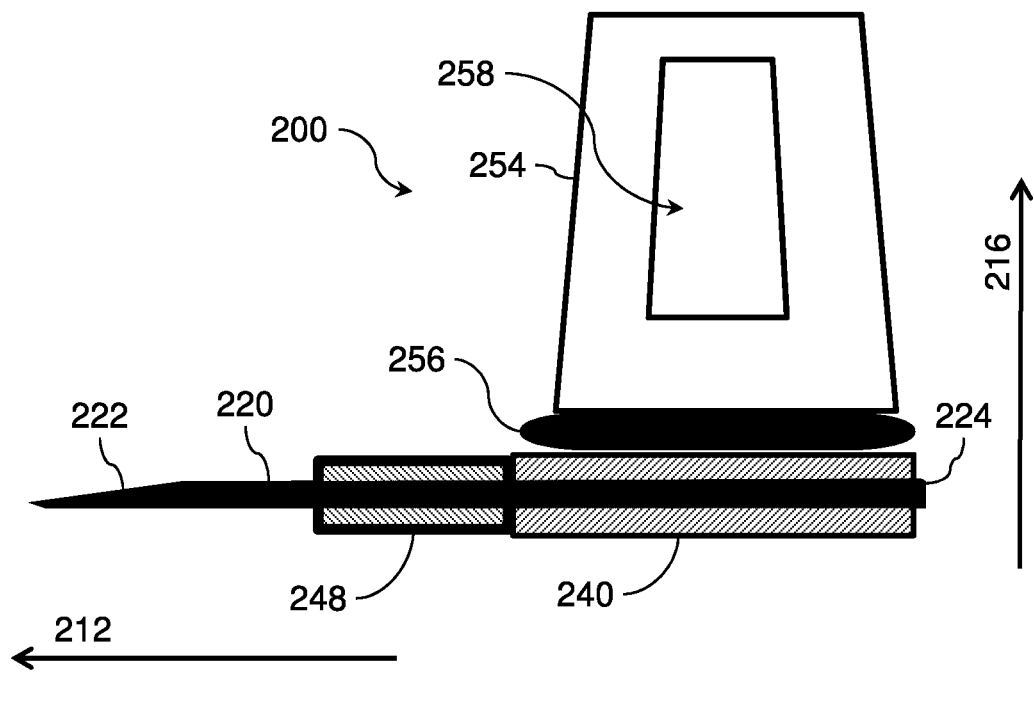
Figure 4:
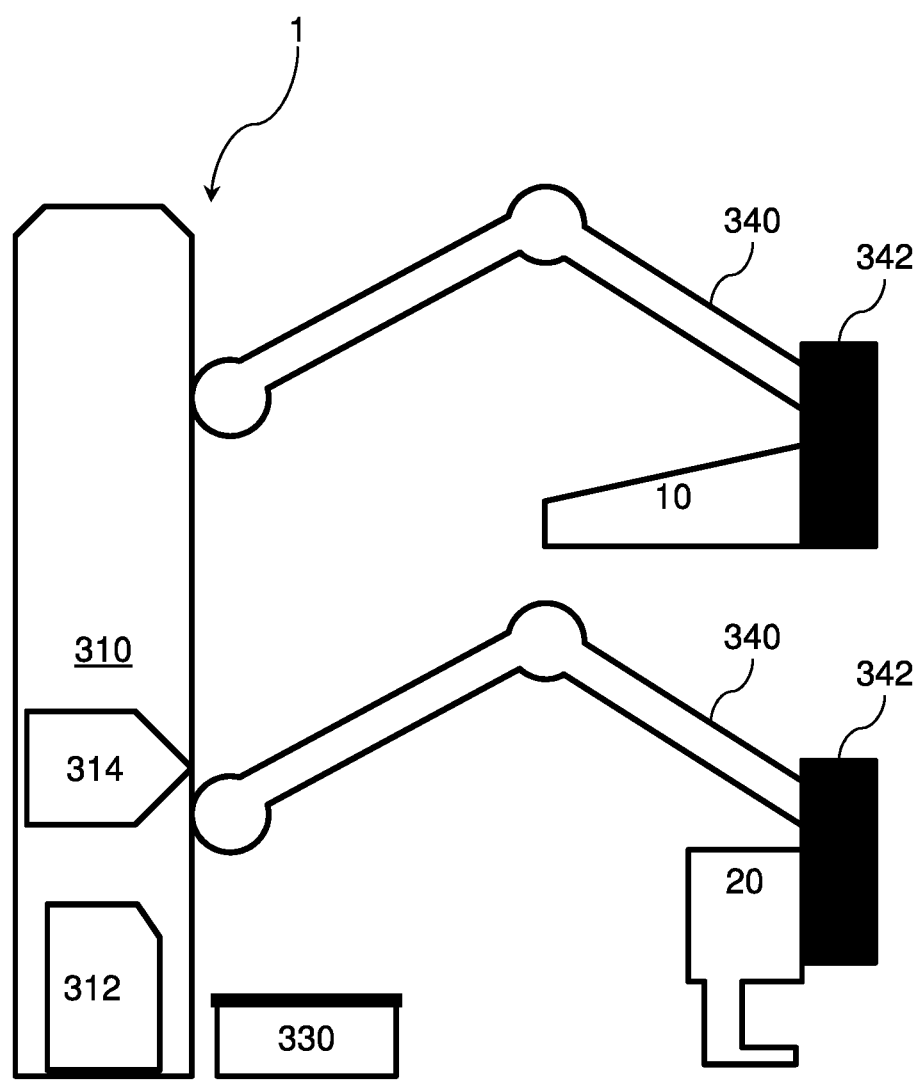
Figure 5:
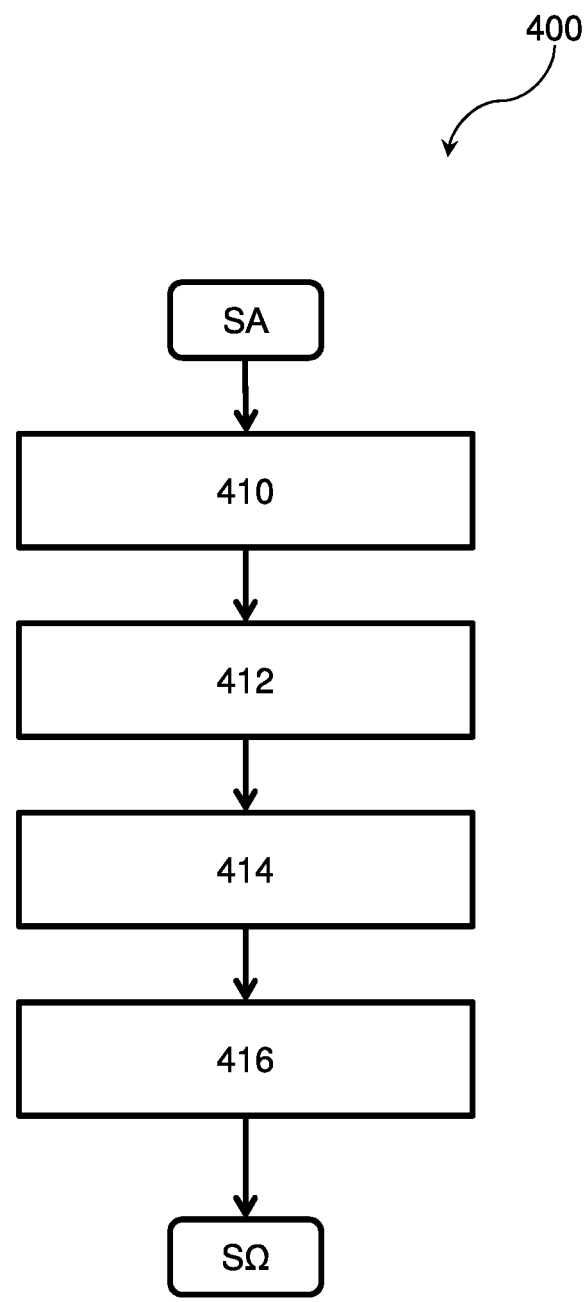

Thereby shown, to some extent schematized:

FIG. 1A a frontal view of a fixing apparatus of an example embodiment of the cannulation robot according to the invention;

FIG. 1B a frontal view of an example embodiment of the cannula holder according to the invention;

FIG. 2 a frontal view of an actuator device of an example embodiment of the cannulation robot according to the invention;

FIG. 3A a frontal view of an example embodiment of the cannula holder according to the invention together with a cannula;

FIG. 3B a side view of said cannula holder;

FIG. 4 an example embodiment of the inventive cannulation robot;

FIG. 5 an example embodiment of the method according to the invention for the automated affixing of a cannula.

FIG. 1A depicts a fixing apparatus of an example embodiment of the cannulation robot according to the invention in a frontal view.

The fixing apparatus 10 comprises an actuator device 100, a positioning device 120 and a fixing base 140. The actuator device 100 and the positioning device 120 are physically connected by the fixing base 140 and thus form one physical unit in which the relative arrangements to one another are predetermined based on the fixation.

The actuator device 100 comprises two actuators 102 and two pressure rods 104, whereby a respective one of said actuators 102 is designed to move a respective one of the pressure rods 104 along an axis of the respective actuator 102 in the direction of a distal end 106 of the respective pressure rod 104. This movement toward the distal end 106 can actuate a guide means. After the actuating of the guide means, the actuators 102 can in particular move the pressure rods 104 again in the opposite direction.

The positioning device 120 is configured to position a cannula holder at an area of a patient's skin at which the cannula is to be affixed. To that end, the positioning device 120 comprises a gripper apparatus 20 and/or is designed to move a gripper apparatus 20 relative to the patient so as to position the cannula holder. Preferably, the positioning device 120 comprises an actuator 122 thereto—in particular an electric actuator—which is physically connected to the fixing base 140 of the fixing apparatus on one side and to the gripper apparatus 20 on the other side. Alternatively or additionally and also preferentially, the fixing apparatus 10, in particular the fixing base 140, can comprise a connecting device 142 by means of which the fixing apparatus 10 can be connected to a robotic tool arm. This enables the fixing apparatus 10 and its gripper apparatus 20, or the gripper apparatus 20 connected thereto respectively, to be moved by the robotic tool arm relative to the patient and thus position the cannula holder.

The gripper apparatus 20 comprises two gripper elements 124 arranged around a receiving area 128 and a moving device 126. The two gripper elements 124 can be moved relative to each other by means of the moving device 126, which preferably has an electric drive, and thus grasp a cannula holder, in particular at one or more grip regions of the cannula holder corresponding to the gripper elements 124 and/or the receiving area 128, by the two gripper elements 124 being moved toward each other.

FIG. 1B shows an example embodiment of a cannula holder according to the invention, in particular for the fixing apparatus of FIG. 1A, as well as a transverse axis 214 and a vertical axis 216 of the cannula holder and/or a cannula connected to the cannula holder, in frontal view. Also illustrated is the position of an upper side 226 and an underside 228 of the cannula holder or cannula respectively.

The cannula holder 200 comprises a base body 240 and two regions 252 for affixing the cannula holder to a patient. Two fixing elements 254 are each physically connected to the base body 240 by means of a respective bearing element 256, wherein the bearing elements 256 support the fixing elements 254 so as to be rotatable about a rotational axis relative to the base body 240. The rotational axis preferably runs, as depicted, at least substantially in the direction of a longitudinal axis of the cannula holder, or cannula respectively, pointing out of the plane of projection. Alternatively and also preferentially, the axis of rotation of the transverse axis 214 runs or at least substantially lies in a plane spanned by the longitudinal axis and the transverse axis. In particular, the fixing elements 254 are configured as wing elements which can be flipped upward relative to the base body 240 in respect of FIG. 1B; i.e. in particular away from the patient, and downward; i.e. in particular toward the patient.

Preferably, the cannula holder 200 is made or consists of plastic and/or produced in an injection molding process. Preferably, the bearing elements 256 are formed as film hinges. Preferably, the cannula holder 200 is made of a disinfectable material, in particular a disinfectable plastic, so that the cannula holder can be disinfected after manufacture and/or after connecting to a cannula.

To connect to a cannula, the cannula holder 200 exhibits a connecting area 242 at which the cannula can be connected, in particular integrally, to the cannula holder. Said connecting area 242 is preferably arranged and configured within or at the base body 240 such that a cannula connected to the cannula holder is rigidly oriented and/or disposed relative to the base body 240, thus in particular the position and/or orientation of the cannula can be dictated by the position and/or orientation of the cannula holder.

To grasp and/or position the cannula, the cannula holder 200 comprises at least one grip region 248. Same is rigidly connected to the base body 240 and/or configured as part of the base body so that the position and/or orientation of the cannula holder can be dictated by a gripper apparatus, in particular by the gripper apparatus 20 from FIG. 1A, which engages with grip region 248. In particular, the grip region 248 can be arranged further forward on the base body 240 or alternatively rearward on the base body 240 in respect of the FIG. 1B plane of projection relative to the regions 252 as depicted. One advantage of this arrangement can be being able to prevent collisions between the regions 252 and the grip region 248 and/or collisions between the respective apparatus for these regions.

In particular, the upper side 226 of the cannula holder is above the base body 240 and its intended position and/or orientation during cannulation, in particular during affixing of the cannula, predetermined and situated opposite the cannula holder's underside 228. The vertical axis 216 thereby extends from the underside 228 to the upper side 226.

The cannula holder 200 and in particular the base body 240 exhibits two longitudinal sides, wherein the transverse axis 214 extends from one of the longitudinal sides to the other of the longitudinal sides. In addition, the transverse axis 214 and the vertical axis 216 enclose an angle of between 45° and 135°, preferably between 70° and 110°, preferably between 80° and 100°, and further preferentially between 86° and 94° and are in particular at least substantially perpendicular to each other. In particular, the transverse axis 214 and the vertical axis 216 in FIG. 1B are at least substantially situated in the plane of projection while the longitudinal axis at least substantially points out of the plane of projection—and thus not depicted in FIGS. 1A and 1B.

Preferably, as depicted, an adhesive 262 is deposited on the respective fixing elements 254 such that the fixing elements 254 are self-adhesive. Alternatively or additionally and also preferentially, a fixing apparatus can comprise a segregating apparatus for adhesive, by means of which an adhesive can be applied onto the fixing elements—the fixing elements 254 can thus in particular be coated with adhesive. The adhesive 262 is in each case deposited on one side of the respective fixing element 254 which, when the fixing element 254 is flipped downward and at least substantially situated on a plane with the base body 240, corresponds to the underside 228 of the cannula holder 200 or is a part of the underside 228 respectively.

The fixing elements 254, or the respective sides of the fixing elements respectively, thereby form an adhesive carrier 260 and the bearing elements 256, in particular together with the fixing elements 254, form a guide means 160, which guides the adhesive carrier 260—i.e. in particular the sides of the fixing elements 254 coated with the adhesive 262—to the skin area of the patient upon being actuated by an actuator device, in particular the actuator device 100 from FIG. 1A. The regions 252 are thus thereby configured as the sides of the fixing elements 254 coated with adhesive.

In particular, the fixing apparatus 10 from FIG. 1A is designed to cooperate with the cannula holder 200 from FIG. 1B and in doing so, secure the cannula holder 200, and in particular a cannula connected to the cannula holder, to an area of skin on a patient. To that end, the gripper apparatus 20 is arranged at the cannula holder 200 such that the grip region 244 is disposed in the receiving area 128. The gripper elements 124 are thereupon moved toward each other and toward the grip region 244 until they engage with one another. The actuator 122, and/or a robotic tool arm with which the fixing apparatus 10 and the gripper apparatus 20 is equipped, positions the cannula holder over the area of the patient's skin at which the cannula holder is to be affixed. The pressure rods 104 of the actuator device 100 are additionally arranged such that when the cannula holder is positioned, the pressure rods 104 are disposed at the fixing elements 254—thus are in particular situated above the fixing elements 254 in FIGS. 1A and 1B. When moved in the direction of their distal end 106, the pressure rods 104 contact a respective fixing element and flip it down to the skin area to come into contact with the sides coated with the adhesive 262—thus regions 252—wherein the movement of these sides—thus the adhesive carrier 260—is guided by the guide means 160—thus in particular the fixing elements 254 and the bearing elements 256.

FIG. 2 depicts an actuator device of one example embodiment of the inventive cannulation robot, in particular a fixing apparatus of the cannulation robot, in frontal view along with a transverse axis 214 and a vertical axis 216. Unless otherwise described and as far as technically feasible, the arrangements, forms, variants and advantages of the present example embodiment in particular correspond to those of the preceding figures. The cannulation robot, the fixing apparatus and/or the actuator device can additionally comprise further components which are not depicted in the figure for the sake of clarity but in particular constitute an integral part of the invention.

Of the actuator device 100, FIG. 2 depicts an actuator 102, two pressure rods 104, a supporting element 110, a rotational bearing 112 and a restoring element 114. The two pressure rods 104 are connected at their proximal ends 108 to the supporting element 110 by means of the rotational bearing 112 and rotatably mounted about a rotational axis which is particular points out of the plane of projection. The pressure rods 104 have a pressing device 116, in particular designed as a roller, at their respective distal ends 106.

The actuator 102 is designed to move the supporting element 110, and thus the pressure rods 104, along an axis of movement, which in particular runs in the direction of or in the opposite direction respectively to the vertical axis 216, toward distal ends 106. Upon the pressing devices 116 encountering mechanical resistance during such movement, in particular a cannula holder and/or an adhesive carrier, the pressing devices 116 move along the mechanical resistance, in particular in a spreading motion. The restoring element 114 thereby counteracts said spreading motion such that the pressing devices 116 press against the mechanical resistance. In particular, the pressing devices, which are in particular designed as rollers, can roll along the mechanical resistance. In particular, the movement along the mechanical resistance can ensue in or opposite to the direction of the transverse axis 214.

FIGS. 3A and 3B depict a further example embodiment of the inventive cannula holder, in particular for a cannulation robot and/or a fixing apparatus with the actuator device from FIG. 2, along with a cannula, a longitudinal axis 212, a transverse axis 214 and a vertical axis 216. Unless otherwise described and as far as technically feasible, the arrangements, forms, variants and advantages of the present example embodiment in particular correspond to those of the preceding figures. The cannula holder can additionally comprise further components which are not depicted in the figures for the sake of clarity but in particular constitute an integral part of the invention.

FIG. 3A shows the cannula holder 200 in a view from the front. The cannula holder 200 comprises a cannula 220 and is connected to same, in particular integrally. The cannula holder 200 additionally comprises a base body 240, a grip region 248, two fixing elements 254—in particular configured as wing elements—, two bearing elements 256 and an adhesive carrier 260.

The two bearing elements 256 are each arranged on a respective longitudinal side of the base body 240 and rotatably support the two wing elements 254 about a rotational axis which in particular points out of the plane of projection. In particular, the transverse axis 214 of the cannula holder 200 extends from one of the longitudinal sides to the other of the longitudinal sides. In particular, the rotational axis points in the direction of the longitudinal axis which in particular points out of the plane of projection and is thus not depicted in this figure.

The adhesive carrier 260 is preferably of two-part configuration and one respective part thereof arranged in each case on one of the two longitudinal sides. The adhesive carrier 260 is thereby connected to a respective one of the longitudinal sides by a respective connecting means 266, in particular welded to the base body 240.

Alternatively to the two-part configuration of the adhesive carrier 260, and also preferentially, the adhesive carrier can also further extend from one longitudinal side to another longitudinal side as a single piece and in particular extend along the underside of the cannula holder, in particular the base body 240, such that an additional adhesive fixing region is disposed on the underside.

The wing elements 254 each have a connecting means 206 for connecting to the adhesive carrier 260. Preferably, the connecting means 206 are designed as engaging elements into which the adhesive carrier 260 is locked into place, preferably detachably. One advantage of such a detachable connection can in particular be that, after the cannula has been affixed, the engaging elements 206 can be disengaged from the adhesive carrier and preferably also removed from the cannula holder 200, in particular by tearing away the bearing elements 256, whereby in particular the comfort of use, thus in particular the comfort when fitted post-cannula fixation can be increased.

FIG. 3B shows the cannula holder 200 with cannula 220 in a side view as a partial cross-section through the base body 240 along longitudinal axis 212. The cannula exhibits a distal end 222 and a proximal end 224, whereby the longitudinal axis 212 of the cannula 220 extends from the proximal end 224 to the distal end 222.

Preferably, the grip region 248 is arranged closer to the distal end 222 than the bearing elements 256 and the wing elements 254 supported by same. This advantageously enables the wing elements to be moved—in particular flipped downward relative to the vertical axis—without colliding with the grip region 248 and a gripper apparatus, in particular the gripper apparatus 20 from FIG. 1A.

The wing elements 254 comprise a respective cavity 258 through which the adhesive carrier—not shown in FIG. 3B—can reach and/or be moved from the respective opposite side of the wing element by an actuator device, in particular the actuator device 100 from FIG. 2. In particular, during their movement along the mechanical resistance, which is formed by the base body 240, the bearing elements 256, the wing elements 254 and the adhesive carrier, the pressing devices 116 of the actuator device 100 from FIG. 2 can reach the adhesive carrier, actuate—i.e. in particular open—the wing elements 254 to the adhesive carrier via connecting means 206, and press the adhesive carrier against the skin area.

FIG. 4 depicts an example embodiment of the inventive cannulation robot, in particular having a fixing apparatus and a gripper apparatus. Unless otherwise described and as far as technically feasible, the arrangements, forms, variants and advantages of the present example embodiment in particular correspond to those of the preceding figures. The cannulation robot, the fixing apparatus and/or the gripper apparatus can additionally comprise further components which are not depicted in the figure for the sake of clarity but in particular constitute an integral part of the invention.

The cannulation robot 1 comprises a fixing apparatus 10, a gripper apparatus 20 and two robotic tool arms 340, wherein one of the tool arms 340 is in each case equipped with the fixing apparatus 10 or the gripper apparatus 20 respectively. In particular, the cannulation robot 1 can alternatively comprise only one tool arm or at least three tool arms. In particular, a tool arm can also be concurrently equipped with two tool devices, in particular the fixing apparatus 10 and the gripper apparatus 20.

The cannulation robot 1 exhibits a central system 310 which accommodates a plurality of cannulation robot components in one common housing and/or provides a stable base for further components of the cannulation robot. The tool arm 340 is thereby affixed to the central system 310 of the cannulation robot 1, whereby its spatial position is dictated at least in regard to its fixation region on the central system 310.

At least one of the tool arms 340 is connected at one end to the central system 310 and exhibits articulated joints as well as a connecting device 342 on the other end which are designed for connecting to a tool device, wherein the joints allow a movement of said tool device relative to the central system 310. Such a tool device can in particular be an embodiment of the fixing apparatus and/or an embodiment of the gripper apparatus.

As illustrated, the gripper apparatus 20 is mechanically connected, in particular in a form-fit and/or force-fit, to the connecting device 342 of one of the tool arms. The cannulation robot 1 is thereby configured to move the gripper apparatus 20 by means of the tool arm 340 to parts of the patient's body so that a cannula held by the gripper apparatus 20 can puncture a blood vessel of said body part and/or a cannula holder connected to the cannula can be positioned at an area of skin, in particular in the proximity of the puncture site, and be affixed to said skin area by means of an adhesive carrier.

As illustrated, a fixing apparatus 10 is mechanically connected, in particular in a form-fit and/or force-fit, to connecting device 342 of one of the tool arms 340. The cannulation robot 1 is thereby configured to move the fixing apparatus 10 by means of the tool arm 340 to parts of the patient's body so that an actuator device of the cannulation robot can actuate a guide means and can affix a cannula by means of an adhesive carrier which guides the guide means to an area of a patient's skin to which the cannula is be affixed.

Preferably, the fixing apparatus 10 corresponds to a fixing apparatus from the preceding figures, whereby it also can comprise the gripper apparatus 20 or is equipped with the tool arm 340 as well as with the fixing apparatus 10 and also the gripper apparatus 20.

Alternatively and preferentially, the cannulation robot 1 exhibits a further embodiment of the fixing apparatus as fixing apparatus 10 or as an additional fixing apparatus.

Said fixing apparatus 10 preferably comprises a segregating apparatus for adhesive carriers which has a storage device for adhesive carriers, wherein the segregating apparatus is designed to sort an adhesive carrier or a part thereof, in particular a section thereof, out of the storage device. Said fixing apparatus also comprises an actuator device and a guide means, wherein the guide means comprises or consists of a transport device, a guide channel and a pressing device, and wherein the transport device is designed to receive the adhesive carrier sorted out by the segregating apparatus and transport it through the guide channel to the pressing device. The actuator device is furthermore designed to move at least the pressing device and the guide channel along the area of the skin to which the cannula is to be affixed. Additionally or alternatively thereto, the actuator device can also be moved along the skin area, in particular via a fixing base of the fixing apparatus and a connecting device of the fixing apparatus having a robotic tool arm, in particular one of the tool arms 340 of the cannulation robot 1. In particular, the fixing apparatus 10 can exhibit said tool arm. Lastly, the pressing device is designed to press on that part of the adhesive carrier disposed between the pressing device and that portion of the skin area over which the actuator device or the tool arm respectively moves the pressing device.

In particular, said fixing apparatus 10 can comprise a positioning device for positioning the cannula holder or, alternatively, the gripper apparatus 20 of the cannulation robot 1, in particular together with one of the tool arms 340 of the cannulation robot 1, can be configured as the positioning device.

Preferably, in particular the fixing apparatus 10, and with it the pressing device, is already moved over the skin area and the adhesive carrier adhered to the skin area prior to the puncturing of the blood vessel; the gripper apparatus 20, which grasps the cannula, is thereupon moved by one of the tool arms 340 of the cannulation robot such that the cannula punctures the blood vessel and the cannula, in particular the cannula holder, then moved to a part of the adhered adhesive carrier and connected thereto, in particular by means of a connecting means of the adhesive carrier and/or the cannula holder.

Preferably, the cannulation robot 1 comprises a storage device 330 designed to store cannula holders, cannulas and/or cannulas with cannula holders. The cannulation robot 1 is thereby preferably designed for a cannula with cannula holder to be removed out of the storage device 330 by being grasped by the gripper apparatus 20.

To control in particular the tool arm device 350 and/or the gripper apparatus 100, the central system 310 preferably comprises a control system 314 which is data-linked to a data processing apparatus 312 of the central system 310. In particular, the data processing apparatus 312 is thereto designed to determine control parameters for program-controlled cannulation. Additionally, the control system 314 is preferably designed to transform these control parameters into control signals and output them for the control, in particular for one of the robotic tool arms 340, the fixing apparatus 10 and/or the gripper apparatus 20.

FIG. 5 depicts an example embodiment of the method according to the invention for the automated affixing of a cannula to a patient in the automated cannulation of a patient blood vessel by means of the cannula, in particular for a cannulation robot and/or for a cannula holder according to one of the preceding figures, in particular for hemodialysis.

The method 400 comprises method steps 410, 412, 414 and 415. The method 400 begins at process start SA and ends at process end SΩ, whereby one or more method steps, in particular a sequence of method steps, and preferably the entire method, can be repeated.

In method step 410, a cannula with a cannula holder is provided or, alternatively, a cannula without a cannula holder is first provided and then connected to a likewise provided cannula holder.

In method step 412, a guide means is actuated by an actuator device, whereby the guide means guides an adhesive carrier to an area of the patient's skin at which the cannula is to be affixed.

In method step 414, the cannula holder, which is connected to the cannula, is positioned at the skin area by a positioning device.

In method step 416, which is in particular realized after the blood vessel has been punctured by the cannula, the cannula is affixed to the skin area by means of the cannula holder and the adhesive carrier. The adhesive carrier thereby in particular adheres to the skin area by means of an adhesive and is connected to the cannula, in particular via the cannula holder or via a tube connected to the cannula.

It is obvious that individual method steps or sequences of the method 400 can also occur in different order when technically feasible. In particular, the order of method steps 412 and 414 depends on the respective cannulation robot, the respective fixing apparatus and/or the respective cannula holder.

In one preferential variant, the adhesive carrier can be adhered to the skin area prior to the cannulation or at least prior to the puncturing of the blood vessel or at least prior to positioning the cannula or cannula holder respectively, whereby said skin area to which the cannula is affixed is already known by virtue of the automated method prior to the puncturing. After the blood vessel has been punctured, the cannula holder is positioned—method step 414—and lastly, the cannula affixed—method step 416. The cannula; i.e. in particular the cannula holder, can thereby be connected to the adhesive carrier such that the adhesive carrier, thus in particular a part thereof, is disposed between the skin area and the cannula holder and the cannula holder is connected to said part of the adhesive carrier, in particular by a connecting means.

In another preferential variant, the blood vessel is first punctured and then the cannula holder positioned—method step 414. The guide means is thereupon actuated by means of the actuator device—method step 412—, whereby the adhesive carrier is guided to the skin area by the guide means. The adhesive carrier is thereby already connected to the cannula holder—in particular the cannula holder can comprise the adhesive carrier—or the adhesive carrier is connected, in particular via the guide means, to the cannula holder and thus the cannula affixed to the skin area—method step 416.

While the preceding describes at least one preferential embodiment, it will be noted that there is a great number of variations thereof. It is also to be noted that the embodiments described only represent non-limiting examples and are not thereby intended to limit the scope, the applicability or the configuration of the systems, apparatus and methods described herein. Rather, the foregoing description will provide a person skilled in the art with guidance for implementing at least one embodiment, wherein it is to be understood that a variety of changes can be made to the functioning and arrangement of the elements described in a preferential embodiment without thereby departing from the subject matter respectively set forth in the accompanying claims nor from legal equivalents thereof.

LIST OF REFERENCE NUMERALS 1 cannulation robot
10 fixing apparatus
20 gripper apparatus
100 actuator device
102 actuator of actuator device
104 pressure rod of actuator device
106 pressure rod distal end
108 pressure rod proximal end
110 actuator device supporting element
112 actuator device rotational bearing
114 actuator device restoring element
116 pressing device
120 positioning device
122 positioning device actuator
124 gripper element
126 gripper apparatus moving device
128 gripper apparatus receiving area
140 fixing base of fixing apparatus
142 fixing apparatus connecting device
160 guide means
200 cannula holder
206 cannula holder connecting means for connecting to an adhesive carrier
212 cannula longitudinal axis
214 cannula transverse axis
216 cannula vertical axis
220 cannula
222 cannula distal end
224 cannula proximal end
226 cannula/cannula holder upper side
228 cannula/cannula holder underside
240 cannula holder base body
242 cannula holder connecting area for connecting to a cannula
248 cannula holder grip region
252 cannula holder regions for affixing to a patient
254 fixing element
256 bearing element
258 cavity at fixing element
260 adhesive carrier
262 adhesive
266 adhesive carrier connecting means for connecting to the cannula holder
310 cannulation robot central system
312 data processing apparatus
314 control system
330 cannulation robot storage device for cannulas and/or cannula holders
340 robotic tool arm
342 tool arm connecting device for connecting to a tool device
400 method for automated securing of a cannula
SA process start
SΩ process end
410 to 416 method steps

The invention claimed is:

1. A cannulation robot for automated affixing of a cannula to a patient for automated cannulation of a blood vessel of the patient, the cannulation robot comprising:
 a fixing apparatus for affixing the cannula to the patient and comprising a segregating apparatus for one or more adhesive carriers, the segregating apparatus comprising a storage device configured to store one or more adhesive carriers and being configured to sort out the one or more adhesive carriers for the affixing of the cannula;

a positioning device designed to position a cannula holder, the cannula holder being a component part of the cannula and/or connected to the cannula, at a skin area of the patient at which the cannula is to be affixed; and an actuator device for a guide designed to guide the one or more adhesive carriers to the skin area, wherein the actuator device is designed to activate the guide and move the one or more adhesive carriers, guided by the guide, toward the skin area, such that the one or more adhesive carriers contacts the skin area as a result of the movement, adheres to the skin area by an adhesive, and is connected to the cannula.

2. The cannulation robot according to claim 1, wherein the fixing apparatus further comprises a connecting device for a robotic tool arm, wherein the connecting device is designed to connect the fixing apparatus to a tool arm of the cannulation robot.

3. The cannulation robot according to claim 1, further comprising a robotic tool arm equipped with at least a gripper apparatus for grasping the cannula, wherein the positioning device is designed to control the robotic tool arm on the basis of one or more motion control parameters and to position the cannula holder, grasped by the gripper apparatus, on the skin area.

4. The cannulation robot according to claim 3, wherein the robotic tool arm is equipped with the gripper apparatus and the fixing apparatus;

the gripper apparatus and the fixing apparatus form a common unit in which the fixing apparatus is arranged adjacent to the gripper apparatus, the gripper apparatus and the fixing apparatus are configured to move in concert by the robotic tool arm, the fixing apparatus comprises the actuator device and the guide, and the guide is arranged adjacent to the actuator device and to the gripper apparatus or the gripper apparatus is designed to dispose the guide adjacent to the actuator device.

5. The cannulation robot according to claim 1, wherein the fixing apparatus comprises the actuator device and the guide, the guide comprises a transport device, a guide channel, and a pressing device, the transport device is designed to transport the one or more adhesive carriers through the guide channel to the pressing device, the actuator device is designed to move at least the pressing device and the guide channel along the skin area to which the cannula is to be affixed, and the pressing device is designed to press on at least a part of the one or more adhesive carriers disposed between the pressing device and that portion of the skin area over which the actuator device respectively moves the pressing device.

6. The cannulation robot according to claim 1, wherein the cannulation robot is configured for connecting (1) the one or more adhesive carriers and (2) a cannula holder holding the cannula, each comprising a connector for connecting to the respective other, the fixing apparatus comprises the actuator device and the guide, the fixing apparatus is designed to adhere the one or more adhesive carriers to the skin area and thereby guide it along the skin area via the guide until, after adhering to the skin area, the one or more adhesive carriers extends over a section of the skin area over which the cannula holder is to be positioned for fixation by the positioning device, and the positioning device is designed to move the cannula holder, after the one or more adhesive carriers adheres to the skin area, toward the one or more adhesive carriers, and connect the two together.

7. The cannulation robot according to claim 3, further comprising the cannula holder, wherein the cannula holder has the one or more adhesive carriers on the underside, the actuator device comprises the positioning device and is designed to move the cannula holder toward the skin area and press the adhesive carrier onto the skin area, guided by the guide.

8. The cannulation robot according to claim 1, further comprising the cannula holder, wherein the cannulation robot is configured to guide the cannula holder with the guide, the guide comprising at least two fixing elements, and a respective bearing element for each respective one of the fixing elements, as the guide secures the cannula to the patient, the actuator device comprises one or more pressure rods, each respectively allocated to one or more of the at least two fixing elements, and an actuator for the pressure rods, and the actuator is designed to actuate the pressure rods, move a distal end of each respective pressure rod to a respectively associated fixing element, and respectively press the fixing element toward the skin area via the pressure rod until the adhesive carrier disposed with the fixing elements touches the skin area.

9. The cannulation robot according to claim 8, wherein the cannula holder comprises a base body, the at least two fixing elements of the cannula holder are designed as wing elements rotatably mounted about a rotational axis relative to the base body by the respective bearing element, the at least two fixing elements comprise respective wing tips that point away from the skin area in an initial state prior to affixing the cannula, and the actuator device is designed to first move the distal ends of the pressure rods toward the base body or toward a respectively associated wing element or its bearing element, and, upon encountering a mechanical resistance, effect a spreading motion by which the distal ends of the pressure rods are in each case moved outwardly away along the associated wing element from the base body.

10. The cannulation robot according to claim 1, wherein the segregating apparatus is further designed to apply the adhesive: onto the adhesive carrier; onto the skin area of the patient; onto the cannula holder; onto a tube connected to the cannula holder; or onto a combination thereof.

11. The cannulation robot according to claim 1, wherein the one or more adhesive carriers comprises at least two different adhesive carriers, the storage device is designed to store the at least two different adhesive carriers, the cannulation robot further comprises a detection system for tissue and/or skin types, which detects data on the nature of the skin area and the tissue underneath by sensor-based measuring of radiation, mechanical forces, and/or chemical substances, and stores the data as tissue and/or skin type identifying data, the cannulation robot is designed to implement a selection process comprising the following steps:

gathering, with the detection system, data on the nature of the skin and the tissue underneath, for the skin area of the patient, at which the cannula is to be affixed;

determining the tissue and/or skin type of the skin area based on the identifying data using a tissue/skin type database;

selecting one of the at least two different adhesive carriers from among the at least two different adhesive carriers, which is suitable for the specific tissue type and/or skin type based on the tissue/skin type database or a different database; and outputting one or more control parameters for the segregating apparatus, wherein at least the segregating apparatus is designed to be controlled, on the basis of the control parameters, to separate out the selected one adhesive carrier.

12. The cannulation robot according to claim 1, further comprising a detection system for detecting a location of the cannula, the detection system being configured to detect location data on the location of the cannula by sensor-based measuring of radiation, mechanical forces, and/or ultrasound, and and being configured to store the location data as cannula location identifying data, wherein the cannulation robot is designed to move the cannula, at a predetermined and minimal displacement and/or force, with the positioning device, after the cannula has been affixed, the detection system is designed to detect a change in location of the cannula upon the movement, and the cannulation robot is designed to determine whether the cannula is sufficiently secured based on the detected change in location of the cannula.

13. A method for the automated affixing of a cannula to a patient for automated cannulation of a blood vessel of the patient, with the cannulation robot according to claim 1, wherein the cannulation robot comprises the cannula and the method comprises the following method steps:

providing the cannula with the cannula holder or providing the cannula without the cannula holder and connecting the cannula to the cannula holder;

providing the fixing apparatus for affixing the cannula to the patient;

sorting out, using the segregating apparatus, the one or more adhesive carriers for the affixing of the cannula;

actuating the guide with the actuator device, wherein the guide guides the one or more adhesive carriers to the skin area at which the cannula is to be affixed;

positioning the cannula holder at the skin area, using the positioning device; and affixing the cannula to the skin area with the cannula holder and the one or more adhesive carriers, wherein the one or more adhesive carriers are adhered to the skin area by an adhesive, and connected to the cannula.

* * * * *